(12) United States Patent
Heaton, II et al.

(10) Patent No.: US 11,564,601 B1
(45) Date of Patent: *Jan. 31, 2023

(54) MULTIDEPTH TISSUE OXIMETER

(71) Applicant: ViOptix, Inc., Newark, CA (US)

(72) Inventors: Larry C. Heaton, II, Pleasanton, CA (US); Robert E. Lash, Redwood City, CA (US); Jimmy Jian-min Mao, Fremont, CA (US)

(73) Assignee: ViOptix, Inc., Newark, CA (US)

( * ) Notice: Subject to any disclaimer, the term of this patent is extended or adjusted under 35 U.S.C. 154(b) by 274 days.

This patent is subject to a terminal disclaimer.

(21) Appl. No.: 16/929,071

(22) Filed: Jul. 14, 2020

Related U.S. Application Data

(60) Continuation of application No. 14/601,174, filed on Jan. 20, 2015, now Pat. No. 10,709,367, which is a division of application No. 12/359,792, filed on Jan. 26, 2009, now Pat. No. 8,938,279.

(51) Int. Cl.
*A61B 5/1455* (2006.01)
*A61B 5/1459* (2006.01)
*A61B 5/06* (2006.01)
*A61B 5/00* (2006.01)

(52) U.S. Cl.
CPC .......... *A61B 5/1459* (2013.01); *A61B 5/0022* (2013.01); *A61B 5/063* (2013.01); *A61B 5/1455* (2013.01); *A61B 5/14551* (2013.01); *A61B 5/14552* (2013.01); *A61B 5/742* (2013.01); *A61B 5/061* (2013.01); *A61B 2562/043* (2013.01)

(58) Field of Classification Search
CPC . A61B 5/0205; A61B 5/1455; A61B 5/14551; A61B 5/14552; A61B 5/1459; A61B 5/742; A61B 5/0022; A61B 5/063; A61B 5/061; A61B 2562/04; A61B 2562/043; A61B 2562/046; A61B 2562/06; A61B 2562/063; A61B 2562/066
See application file for complete search history.

(56) References Cited

U.S. PATENT DOCUMENTS

| | | |
|---|---|---|
| 3,874,781 A | 4/1975 | Thiel |
| 4,408,353 A | 10/1983 | Bowen et al. |
| 4,884,095 A | 11/1989 | Yamanouchi et al. |
| 4,910,539 A | 3/1990 | Mathis et al. |

(Continued)

FOREIGN PATENT DOCUMENTS

| | | |
|---|---|---|
| EP | 0476596 | 3/1992 |
| EP | 0800099 | 8/1997 |

(Continued)

OTHER PUBLICATIONS

H. Taitelbaum et al., "Approximate theory of photon migration in a two-layer medium", Applied Optics, 28(12), 2245, 1989.

(Continued)

*Primary Examiner* — Chu Chuan Liu
(74) *Attorney, Agent, or Firm* — Aka Chan LLP

(57) ABSTRACT

An oximeter measures oxygen saturation for two or more different tissue depths and shows these results on a screen. A probe of the oximeter has multiple different distances between source and detector sensors. One probe implementation has fixed sensor positions. Other implementations include sensors on a moveable platform or openings to accept sensors, which allow a user to vary a distance between sensors.

44 Claims, 14 Drawing Sheets

(56) References Cited

U.S. PATENT DOCUMENTS

| | | |
|---|---|---|
| 5,031,984 A | 7/1991 | Eide et al. |
| 5,069,214 A | 12/1991 | Samaras et al. |
| 5,088,493 A | 2/1992 | Giannini et al. |
| 5,212,748 A | 5/1993 | Curtiss et al. |
| 5,224,478 A | 7/1993 | Sakai et al. |
| 5,339,375 A | 8/1994 | Kerns |
| 5,400,421 A | 3/1995 | Takahashi |
| 5,482,034 A | 1/1996 | Lewis et al. |
| 5,524,617 A | 6/1996 | Mannheimer |
| 5,548,672 A | 8/1996 | Hattori et al. |
| 5,584,296 A | 12/1996 | Cui et al. |
| 5,754,716 A | 5/1998 | Kim et al. |
| 5,879,294 A | 3/1999 | Anderson et al. |
| 5,978,534 A | 11/1999 | O'Rourke et al. |
| 6,078,833 A | 6/2000 | Hueber |
| 6,263,221 B1 | 7/2001 | Chance |
| 6,282,339 B1 | 8/2001 | Zheng |
| 6,285,904 B1 | 9/2001 | Weber et al. |
| 6,353,226 B1 | 3/2002 | Khalil et al. |
| 6,424,774 B1 | 7/2002 | Takeda et al. |
| 6,487,343 B1 | 11/2002 | Lewandowski et al. |
| 6,516,209 B2 | 2/2003 | Cheng et al. |
| 6,549,284 B1 | 4/2003 | Boas et al. |
| 6,587,703 B2 | 7/2003 | Cheng et al. |
| 6,597,931 B1 | 7/2003 | Cheng et al. |
| 6,615,065 B1 | 9/2003 | Barrett et al. |
| 6,667,803 B1 | 12/2003 | Flessland et al. |
| 6,671,526 B1 | 12/2003 | Aoyagi et al. |
| 6,708,048 B1 | 3/2004 | Chance |
| 6,735,458 B2 | 5/2004 | Cheng et al. |
| 6,801,648 B2 | 10/2004 | Cheng |
| 6,859,658 B1 | 2/2005 | Krug |
| 6,892,006 B2 | 5/2005 | Lewandowski et al. |
| 7,247,142 B1 | 7/2007 | Elmandjra et al. |
| 7,254,427 B2 | 8/2007 | Cho et al. |
| 7,355,688 B2 | 4/2008 | Lash et al. |
| 7,551,950 B2 | 6/2009 | Cheng |
| 9,398,870 B2 | 7/2016 | Bechtel et al. |
| 2003/0144583 A1 | 7/2003 | Cheng et al. |
| 2004/0111016 A1 | 6/2004 | Casscells et al. |
| 2005/0228595 A1 | 10/2005 | Cooke et al. |
| 2006/0074282 A1 | 4/2006 | Ward et al. |
| 2006/0106293 A1 | 5/2006 | Fantini |
| 2006/0155193 A1 | 7/2006 | Leonardi et al. |
| 2007/0055119 A1 | 3/2007 | Lash et al. |
| 2007/0149865 A1 | 6/2007 | Laakkonen |
| 2008/0300474 A1 | 12/2008 | Benni et al. |
| 2010/0256461 A1 | 10/2010 | Mohamedali et al. |

FOREIGN PATENT DOCUMENTS

| | | |
|---|---|---|
| EP | 0816829 | 7/1998 |
| GB | 1386734 | 3/1975 |
| GB | 1558643 | 9/1980 |
| WO | 2006113394 | 10/2006 |

OTHER PUBLICATIONS

E. Okada et al., "Theoretical and experimental investigation of near-infrared light propagation in a model of the adult head", Applied Optics, vol. 36, No. 1, p. 21-31, 1997.

D. Hueber et al., "New Optical Probe Designs for Absolute (Self-Calibrating) NIR Tissue Hemoglobin Measurements," Proceedings of Optical Tomography and Spectroscopy of Tissue III, Jan. 1999, 618-631, vol. 3597.

B. Chance et al., "New Optical Probe Designs for Absolute (Self-Calibrating) NIR Tissue Hemoglobin Measurements", Proceedings of Optical Tomography and Spectroscopy of Tissue III, Jan. 24-28, 1999, San Jose, California, vol. 3597, pp. 618-631.

E. Lee et al., "Correlation of Cerebral Oximetry Measurement with Carotid Artery Stump Pressures During Carotid Endarterectomy", Vasc. Endovascular Surg. 2000, Sep./Oct. 2000, vol. 34, No. 5, pp. 403-409.

MULTIDEPTH TISSUE OXIMETER

CROSS-REFERENCE TO RELATED APPLICATIONS

This patent application is a continuation of U.S. patent application Ser. No. 14/601,174, filed Jan. 20, 2015, issued as U.S. Pat. No. 10,709,367 on Jul. 14, 2020, which is a divisional of U.S. patent application Ser. No. 12/359,792, filed Jan. 26, 2009, issued as U.S. Pat. No. 8,938,279 on Jan. 20, 2015. These applications are incorporated by reference along with all other references cited in this application.

BACKGROUND OF THE INVENTION

The present invention relates to the field of medical devices, and more specifically, to a multidepth tissue oximeter.

Medical devices are among the marvels of modern medicine. Doctors and people use medical devices to help treat patients who suffer from injuries, diseases, and the consequences of old age. Some revolutionary medical devices include the balloon catheter, oximeter, stent, and shunt. Over the years, these have improved the lives of many millions of people—allowing them to live better, longer, and more fulfilling lives.

Medical devices continue to evolve and improve. Today's medical devices are more durable, dependable, and easier to use than those introduced just a few years ago.

Despite the widespread success of current medical devices, there is a need for new and improved medical devices that provide greater features and functionality, and devices which generally help improve the lives of human beings and other animals.

Oximeters are medical devices used to measure oxygen saturation of tissue in patients. Typically, an oximeter takes a measurement at a single depth below the surface of the tissue. For some medical procedures such as buried flap monitoring, abdominal organ tissue oxygenation measurement, and cerebral oxygenation measurement, it is important to obtain oxygen saturation readings at numerous depths below the surface of the tissue.

However, the typical oximeter does not measure oxygen saturation at numerous depths. Moreover, the typical oximeter is not capable of targeting specific regions or specific layers of tissue. This can result in inaccurate readings of the oxygen saturation for the desired layer of tissue to be measured.

Therefore, there is a need to provide improved tissue oximeter systems and techniques.

BRIEF SUMMARY OF THE INVENTION

An oximeter measures oxygen saturation for two or more different tissue depths and shows these results on a screen. A probe of the oximeter has multiple different distances between source and detector sensors. One probe implementation has fixed sensor positions. Other implementations include sensors on a moveable platform or openings to accept sensors, which allow a user to vary a distance between sensors.

In an implementation, a multidepth tissue oximeter has four, six, or eight light detectors. When there are four (six or eight) detectors, there are two (three or four) colored curves shown on the console screen for trend of oxygen saturation (StO2) at different depths, i.e. at different tissue layers. The current oxygen saturation values at different tissue depth are shown on the screen by two (three or four) colored numbers. There is option to show only one curve and one number for the tissue depth in interest. There are four laser sources: two of them emit light of wavelength 690 nanometers and the other two emit 830 nanometers. The console has a connector for the sensor to be connected.

Three different designs of probe are described. One design has source-detector separation on probe surface is fixed. A probe of a multidepth tissue oximeter has two light apertures and at least four detector apertures. The light source apertures are for optical fibers that connected through optical fiber to laser diodes within the console. A part of detector apertures, which are nearer the light source apertures are for optical fibers running to the photodiodes within the console. The remaining detector apertures, which are further away from the light source apertures, are for photodiodes or photodetectors. These photodetectors are connected to the console via electrical wires rather than fiber.

Further, photodiodes in probe further away from the source apertures may be open to air. Photodiodes nearer the source apertures can be covered with grey or dark film to shield light arriving photodiode.

Another probe design for multidepth tissue oximetry is that the distance from the sources and detectors can be mechanically adjusted by the use. One approach is a combination of one source and two detectors, or combinations of more sources and more detectors. The source-detector separation can be adjusted by steps or continuously.

In a design the source-detector, separation is adjustable by mechanical distance steps, where a positioning pin slips into one of a series of predefined distance notches.

Another probe design for multidepth tissue oximetry provides source-detector separation that is adjustable continuously. A technique of distance measurement sensing may be incorporated in the probe. For example, the probe can include a linear distance measurement transducer. In an implementation, the probe has a source-detector separation that is adjustable continuously adjustable by the user. There can be markings for measuring the separation.

A multidepth oximeter can be applied to buried flap monitoring, abdominal organ tissue oxygenation measurement (e.g., liver, kidney, or bowel), and cerebral oxygenation measurement. A specific multidepth oximeter can measure tissue at depths 0.5, 2, or 4 centimeters, or any combination of these.

A probe could include a source and detector arrangement where there is only one detector pair but multiple source pairs (e.g., two source pairs, three source pairs, four source pairs, or more than four source pairs). Typically, photodiodes are more expensive than LEDs and laser diodes. Thus, minimizing the number of photodiodes can lower the cost of a probe. The detectors may not be shaded (e.g., covered with a light shading film). Different source pairs may emit lights of different intensity. The source pair near (or nearest) the detector pair may emit the lowest intensity of light.

Alternatively, a probe could include one source pair only, but multiple detector pairs. Some of the detectors may be covered with a shading film. A probe can include two separate films, one darker and the other lighter.

In a specific implementation, a probe includes moveable sources, detectors, or both. The algorithm (or system) can know or determine the present distance between the source and the detector when the source, detector, or both are moving or have been moved. For example, in a specific implementation, the probe includes a moveable platform that moves along a track. The track of the movable platform may use material with detectable resistance. When the structure (or moveable platform) is moving along the track, the resistance changes and indicates the location of the moveable platform and therefore the source and detector separation.

In another implementation, a probe with moveable sensors (e.g., sources or detectors) includes holes to removably connect a sensor. There is a mechanism of electronic detection of the source and detector separation. Each hole may serve as an electric switch: when sensors are in the holes, the switches for the holes are on and therefore the system knows which holes are holding the sensors (or source fibers or detector fibers).

In an embodiment, a method includes calculating a first oxygen saturation measurement for a tissue at a first depth below a tissue surface, calculating a second oxygen saturation measurement for the tissue at a second depth below the tissue surface, where the second depth is beneath the first depth, displaying a first value indicative of the first oxygen saturation measurement at a first position on a screen, and displaying a second value indicative the second oxygen saturation measurement at a second position on the screen.

The first value may include a first number and the second value may include a second number. The first value may include a first curve displayed in a first color and the second value may include a second curve displayed in a second color, different from the first color.

The method may further include repeatedly alternating between the calculating a first oxygen saturation measurement and the calculating a second oxygen saturation measurement to provide real-time first and second values. The first and second curves may be displayed concurrently and superimposed on each other.

In an embodiment, the method further includes displaying a first warning indicator on the screen if the first oxygen saturation measurement drops below a first threshold value, and displaying a second warning indicator on the screen if the second oxygen saturation measurement drops below a second threshold value. Displaying the first warning indicator may include causing the first value to be displayed differently.

In a specific embodiment, a device includes a first structure of a first type, a second structure of the first type, a third structure of a second type, a fourth structure of the second type, a fifth structure of the second type, and a sixth structure of the second type, where a first distance extends between the first structure and the third structure without touching the second structure or the fifth structure, a second distance extends between the second structure and the fourth structure without touching the first structure or sixth structure, the first distance is different from the second distance, and a third distance extends between the first structure and the fifth structure, a fourth distance extends between the second structure and the sixth structure, and the third distance is different from the fourth distance.

The second distance may be greater than the first distance, and the fourth distance may be greater than the third distance. A first line passing through the third and fourth structures may be parallel to a second line passing through the fifth and sixth structures. A third line passing through the first and second structures may not be parallel to the first line. A first line passing through the first, third, and fifth structures may be parallel with a second line passing through the second, fourth, and sixth structures.

In a specific embodiment, the first type of structure is a source and the second type of structure is a detector. In another embodiment, the first type of structure is a detector and the second type of structure is a source.

In an embodiment, a probe includes a first plurality of structures of a first type along a first edge of the device, a second plurality of structures of a second type, a third plurality of structures of the second type along a second edge of the device, opposite the first edge, where the second plurality of structures is between the first plurality of structures and the third plurality of structures.

In an embodiment, a device includes a first structure of a first type, a second structure of the first type, a third structure of a second type, a fourth structure of the second type, a fifth structure of the second type, and a sixth structure of the second type, where a first distance extends between the first structure and the third structure without touching the second structure or the fifth structure, a second distance extends between the second structure and the fourth structure without touching the first structure or sixth structure, and a light shading film covers the third and fourth structures.

The light shading film may not cover the first, second, fifth, and sixth structures.

In an embodiment, a device includes a first structure of a first type, a second structure of the first type, a third structure of a second type, a fourth structure of the second type, a fifth structure of a third type, and a sixth structure of the third type, where a first distance extends between the first structure and the third structure without touching the second structure or the fifth structure, a second distance extends between the second structure and the fourth structure without touching the first structure or sixth structure.

The second type of structure may include optical fiber and the third type of structure may include a photodetector.

In an embodiment, a device includes a first structure of a first type, a second structure of a second type, and a third structure of the second type, where the second type of structure comprises an opening to removably couple a sensor.

The sensor may include optical fiber. The sensor may include a photodiode. The first, second, and third structures may form a line.

In an embodiment, a probe includes a first structure of a first type, a first movable platform, and a second structure of a second type, positioned on the first movable platform.

The probe may further include a second movable platform, where the structure of the first type is position on the second movable platform. In another embodiment, the first structure is positioned at a fixed position of the probe. The probe may further include graduated markings between the first and second structures.

In an embodiment, a device includes a probe including a first plurality of structures of a first type, a second plurality of structures of a second type, and a third plurality of structures of the second type, where the second plurality of structures is between the first plurality of structures and the third plurality of structures, and a multiplexing block, connected to the second and third plurality of structures.

The device may include a plurality of emitters, connected to the first plurality of structures, a plurality of photodetectors, connected to the multiplexing block, and a control block, coupled to the multiplexing block.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
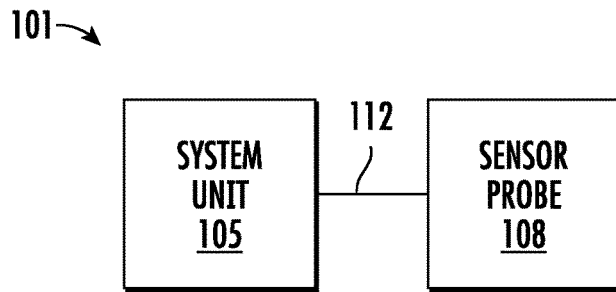
FIG. 1 shows a block diagram of an oximeter system for measuring oxygen saturation of tissue in a patient.

FIG. 1 shows an oximeter system 101 for measuring oxygen saturation of tissue in a patient. The system includes a system unit 105 and a sensor probe 108, which is connected to the system unit via a connection 112. Connection 112 may be an electrical, optical, or another wired connection including any number of wires (e.g., one, two, three, four, five, six, or more than six wires or optical fibers), or any combination of these or other types of connections. In other implementations of the invention, however, connection 112 may be wireless such as via a radio frequency (RF) or infrared communication.

Typically, the system is used by placing the sensor probe in contact or close proximity to tissue (e.g., skin or nerve) at a site where an oxygen saturation or other related measurement is desired. The system unit causes an input signal to be emitted by the sensor probe into the tissue (e.g., human tissue). There may be multiple input signals. These signals may have varying or different wavelengths. The input signal is transmitted into or through the tissue.

Then, after transmission through or reflection off the tissue, the signal is received at the sensor probe. This received signal is received and analyzed by the system unit. Based on the received signal, the system unit determines the oxygen saturation of the tissue and displays a value on a display of the system unit.

In an implementation, the system is a tissue oximeter, which can measure oxygen saturation without requiring a pulse or heartbeat. A tissue oximeter of the invention is applicable to many areas of medicine and surgery including plastic surgery and spinal surgery. The tissue oximeter can make oxygen saturation measurements of tissue where there is no pulse; such tissue, for example, may have been separated from the body (e.g., a flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbances of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. These patents are assigned to the same assignee as this patent application and are incorporated by reference.

Figure 2:
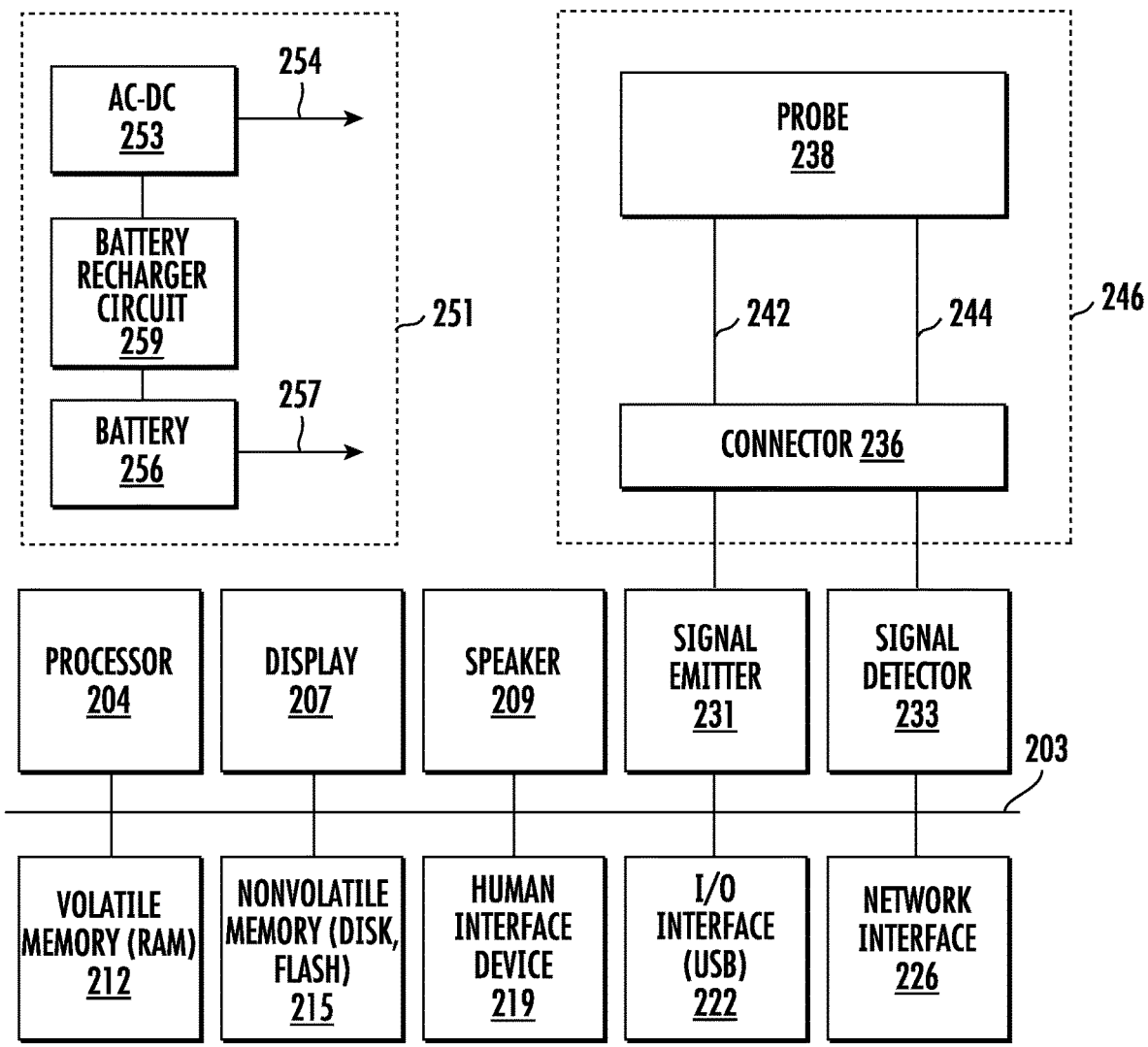
FIG. 2 shows a more detailed block diagram of a specific implementation of the system of FIG. 1.

FIG. 2 shows greater detail of a specific implementation of the system of FIG. 1. The system includes a processor 204, display 207, speaker 209, signal emitter 231, signal detector 233, volatile memory 212, nonvolatile memory 215, human interface device or HID 219, I/O interface 222, and network interface 226. These components are housed within a system unit enclosure. Different implementations of the system may include any number of the components described, in any combination or configuration, and may also include other components not shown.

The components are linked together using a bus 203, which represents the system bus architecture of the system. Although this figure shows one bus that connects to each component, the busing is illustrative of any interconnection scheme serving to link the subsystems. For example, speaker 209 could be connected to the other subsystems through a port or have an internal direct connection to processor 204.

A sensor probe 246 of the system includes a probe 238 and connector 236. The probe is connected to the connector using wires 242 and 244. The connector removably connects the probe and its wires to the signal emitter and signal detectors in the system unit. There is one cable or set of cables 242 to connect to the signal emitter, and one cable or set of cables 244 to connect to the signal detector. In an implementation the cables are fiber optic cables, but in other implementations, the cables are electrical wires. In a specific implementation, the cables include fiber optic cables and electrical wires.

Signal emitter 231 is a light source that emits light at one or more specific wavelengths. In a specific implementation, two wavelengths of light (e.g., 690 nanometers and 830 nanometers) are used. In other implementations, other wavelengths of light may be used. The signal emitter is typically implemented using a laser diode or light emitting diode (LED). Signal detector 233 is typically a photodetector capable of detecting the light at the wavelengths produced by the signal emitter.

The connector may have a locking feature; e.g., insert connector, and then twist or screw to lock. If so, the connector is more securely held to the system unit and it will need to be unlocked before it can be removed. This will help prevent accidental removal of the probe.

The connector may also have a first keying feature, so that the connector can only be inserted into a connector receptacle of the system unit in one or more specific orientations. This will ensure that proper connections are made.

The connector may also have a second keying feature that provides an indication to the system unit which type of probe is attached. The system unit may handle making measurements for a number of different types of probes. When a probe is inserted, the system uses the second keying feature to determine which type of probe is connected to the system. Then the system can perform the appropriate functions, use the proper algorithms, or otherwise make adjustments in its operation for the specific probe type.

For example, when the system detects a cerebral probe is connected, the system uses cerebral probe algorithms and operation. When the system detects a thenar probe is connected, the system uses thenar probe algorithms and operation. A system can handle any number of different types of probes. There may be different probes for measuring different parts of the body, or different sizes or versions of a probe for measuring a part of the body (e.g., three different thenar probe models).

With the second keying feature, the system will be able to distinguish between the different probes. The second keying feature can use any type of coding system to represent each probe including binary coding. For example, for a probe, there are four second keying inputs, each of which can be a logic 0 or 1. With four second keying inputs, the system will be able to distinguish between sixteen different probes.

Typically, probe 246 is a handheld tool and a user moves the probe from one point to another to make measurements. However, in some applications, probe 246 is part of an endoscopic instrument or robotic instrument, or both. For example, the probe is moved or operated using a guiding interface, which may or may not include haptic technology.

In various implementations, the system is powered using a wall outlet or battery powered, or both. Block 251 shows a power block of the system having both AC and battery power options. In an implementation, the system includes an AC-DC converter 253. The converter takes AC power from a wall socket, converts AC power to DC power, and the DC output is connected to the components of the system needing power (indicated by an arrow 254). In an implementation, the system is battery operated. The DC output of a battery 256 is connected to the components of the system needing power (indicated by an arrow 257). The battery is recharged using a recharger circuit 259, which received DC power from an AC-DC converter. The AC-DC converter and recharger circuit may be combined into a single circuit.

The nonvolatile memory may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

The processor may include multiple processors or a multicore processor, which may permit parallel processing of information. Further, the system may also be part of a distributed environment. In a distributed environment, individual systems are connected to a network and are available to lend resources to another system in the network as needed. For example, a single system unit may be used to collect results from numerous sensor probes at different locations.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

Further, a computer-implemented or computer-executable version (e.g., computer program product) of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, Matlab (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows 7, Windows CE, Windows Mobile), Linux, HP-UX, UNIX, Sun OS, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may interface to other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or other device (e.g., laptop computer, smartphone, or personal digital assistant), a user accesses a system of the invention through a network such as the Internet. The user will be able to see the data being gathered by the machine. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 3:
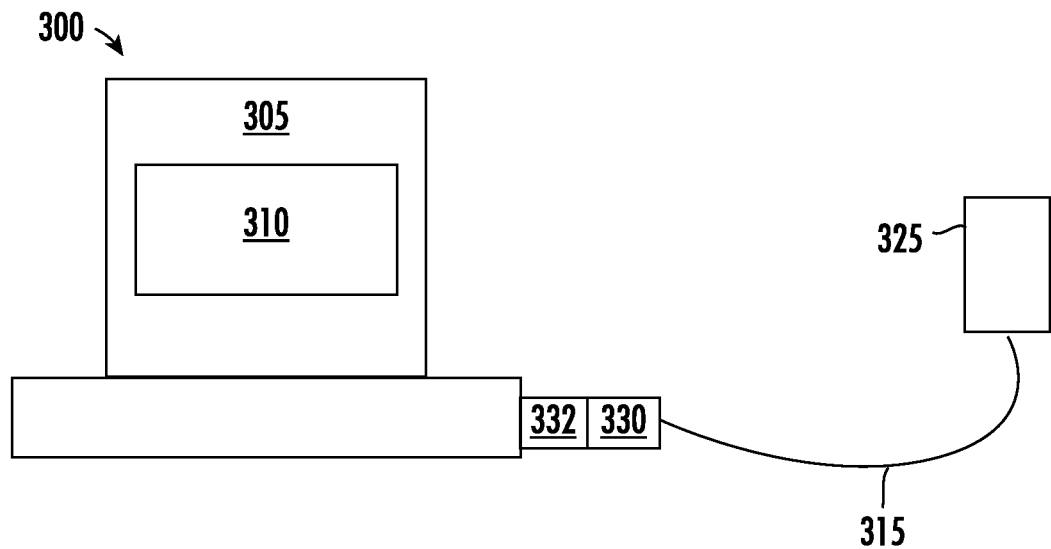
FIG. 3 shows a block diagram of a probe connected to a monitoring console.

FIG. 3 shows a system 300 of the invention including a monitoring console 305 having a display 310 and a cable 315, which connects a probe 325 to the monitoring console via a connector 330 at an end of the cable and a connector 332 on the monitoring console. The probe may include a sensor unit (i.e., sensor head) that is at least partially encased in a sensor housing.

The length of the cable may vary. In a specific implementation, the length of the cable ranges from about 1.2 meters to about 3 meters. For example, the cable may be about 1.3, 1.4, 1.5, 1.6, 1.7, 1.8, 1.9, 2, 2.1, 2.2, 2.3, 2.4, or 2.5 meters long or greater. Depending on the specific application, the length of the cable may be less than 1.2 meters or greater than 3 meters.

A specific application of the invention is operating room use or other places where it is desirable to maintain cleanliness and sterile conditions, such as isolation units. Patients in isolation units may have contagious diseases or compromised immune systems. Hospitals need to ensure that patients with a contagious disease do not infect others. Items introduced near the patient must either be disposed after use or properly cleaned. Hospitals also need to protect patients with compromised immune systems from sources of microorganisms. In these cases, a longer length of cable, such as greater than 1.2 meters, is advantageous because this helps to separate the patient from sources of contamination, such as the console. Similarly, a longer cable length also minimizes contamination, such as contamination of the console, by the patient.

The probe including the sensor housing and sensor head, entire length of cable and the connector are packaged as a probe unit in a package that is sealed using, for example, an adhesive, heat (e.g., heat sealing) or a vacuum (e.g., vacuum sealing). The sealing helps to prevent bacteria and debris from entering the inside of the package and maintains a sterile environment for the contents (e.g., sensor housing, sensor unit, and cables).

The probe unit is detachable from the console after use and may be disposed. A user may then open a new package containing a new probe unit. The package may be opened at the time of actual use or near the time of actual use so as to not contaminate the probe unit. The user can then connect this new and sterile probe unit to the console to begin monitoring. This disposable feature provides an additional level of protection in maintaining a sterile field around the patient.

In some cases, short cables pose a problem. Short cables bring whatever element they are connected to within close proximity to the patient. Doctors and nurses must then devote additional care and time to ensure a sterile field around the patient. This may include, for example, additional cleansing of the elements before and after introduction to the sterile field, or sterile drapes on the elements.

In a specific embodiment, there are other connectors on the cable besides connector 330. These other connectors allow the cable to be separated into two or more pieces. The cable pieces attached to the probe may then be disposed along with the probe after use. The cable pieces attached to the console may be reused. Thus, those pieces of cables most likely to become contaminated such as those cable pieces that are connected to the probe and that will be nearer the patient, can be disconnected from those cable pieces further away from the patient (i.e., the cable pieces connected to the console). This can reduce costs because only a portion of the cable is disposed while the other portion is reusable.

The cable may include optical wave guides, electrical wires, or both.

The optical wave guides transmit light from the console, to the probe, and into the tissue, transmit light from the tissue to the console, or both. In this specific implementation, the cable is passive. For example, it will not contain any active, generative properties to maintain signal integrity. However, in other implementations, cable includes active components. These active components may be used amplify the signal transmitted from the console to the sensor unit, amplify the single transmitted from the sensor unit to the console, or both. For example, long lengths of cable subject to significant attenuation may require amplification. Amplification may also be required if the monitored site contains a particularly dense structure such as bone. In a specific implementation, radiation sources such as light emitting diodes (LEDs) may be placed in the probe. Thus, the cable may contain electrical wiring to transmit power to the radiation sources.

Typically, the electrical wires are standard electrical wiring (e.g., copper or aluminum wire), which is stranded or solid core, or coaxial cable, or any combination of these. The electrical wires are generally used to transmit a signal (e.g., current or voltage) at the probe to the console. In this specific implementation, the electrical wires are connected to photodiodes in the sensor which detect light transmitted from the tissue. The photodiodes generate a signal which is then transmitted to the console via the electrical wires.

In another implementation, the electrical wires are used to transmit a signal from the console to the probe. For example, the probe may include LEDs that are connected to the console via the electrical wires.

In a specific implementation, the cable is enclosed in a flexible cable jacket. The flexible cable jacket may be thin-walled polyvinyl chloride (PVC) with or without an aluminum helical monocoil, shrink wrap tubing, plastic, rubber, or vinyl. In this specific implementation, as shown in the example of FIG. 3, the flexible cable jacket includes both optical fiber and electrical wiring. However, in another implementation, there are at least two flexible cable jackets and the optical fibers are enclosed their own flexible cable jacket while the electrical wires are enclosed in another flexible cable jacket.

In a specific embodiment, all of the optical fibers are enclosed within one end, or both ends of the flexible cable jacket. Minimizing the number of exposed cables lowers the likelihood that the cables will get entangled. In another embodiment, the optical fibers are not enclosed together and instead each optical fiber is enclosed in its own flexible cable jacket.

In an implementation, the connectors on the cable and monitoring console have indicators. The indicators may be color indicators that are painted on, or raised indicators, or both. These indicators help the user to properly attach the cable to the monitoring console. For example, the indicators may include green arrows placed on connectors 332 and 330. Alignment of the arrows indicates proper attachment of the cables. Further, there may be instructions printed on the console, cables, or both that instruct the user on the proper attachment of the cable.

The connector at the end of the cable attaches to the monitoring console and protects the cable from becoming accidentally disconnected. The connector may be a threaded collar on a cable end that threads onto the connector on the monitoring console. Alternatively, the connector may be a lug closure, press-fit, or snap-fit. In a specific embodiment, the connector is designed to be permanently connected to the console and not removable by the user. That is, the sensor head and cable are designed to be reusable. In this specific embodiment, after the probe is used, the sensor housing is removed from the sensor head and a new sensor housing is placed over the sensor head.

In an implementation, the monitoring console is portable. Thus, the console can be hand-carried or mounted to an intravenous (IV) pole. A portable console can follow a patient anywhere in the hospital, eliminating the need to change connections whenever a patient is moved. Moreover, a portable design facilitates use and assessments in numerous other locations besides a hospital.

A portable console is typically battery-operated. The battery is typically a rechargeable type and may have any type of rechargeable battery chemistry. Some examples of rechargeable battery chemistries include nickel cadmium (NiCd), nickel metal hydride (NiMH), lithium ion (Li-Ion), lithium polymer, and lead acid. The system can operate for a certain amount of time on a single battery charge. After the battery is drained, it may be recharged and then used again.

The portable console may also have a power-saving feature. This reduces battery consumption during continuous measurements. The power-saving feature may, for example, darken the console's display screen after a certain time of inactivity. The time may be approximately five, ten, fifteen, or twenty minutes. Alternatively, the user may program the time.

In a specific implementation, the portable console weighs approximately 4.3 kilograms. However, the weight may vary from about 3 kilograms to about 7 kilograms including, for example, 3.5, 4, 4.5, 5, 5.5, 6, 6.5, or more than 7 kilograms.

In another implementation, the console is not hand-held or portable. The console may be a large, nonportable device that is attached to a wall or secured to a stand or surface. In this implementation, the system is typically connected to AC power. A battery may be used as a back-up to the AC power.

In a specific implementation, the console provides alerts. The alerts may be visual (e.g., a flashing light on a display of the console), audible, or both. Visual alerts may be designed so that they are viewable from any location (e.g., a flashing light on the top of the console). In a chaotic and noisy situation, this allows users to quickly respond to a patient. These alerts may signal a problem with the system. This includes, for example, insufficient signal strength, kinks or sharp bends in the cable, debris on the sensor unit, debris on a coupling surface between the cable and the console, insufficient electrical power, a low battery, an improperly attached cable, or other problem.

An alert may also signal when the system is ready for patient monitoring. The alerts may also provide warnings at certain oxygen saturation levels. Different alerts may be used depending on the type of problem detected by the system. Different alerts include different colors, sounds, and intensities of colors and sounds.

The console may provide an alert when the probe is placed in a suitable location for a measurement. The alert may vary in intensity depending on the suitability of the location. The alert may be audible, or visual, or both. An audible alert allows the user to determine the suitability of a location without having to look away from the patient.

The alerts may be user-programmable. That is, users may set which alerts are enabled, the threshold at which they are activated, and the intensities of the alerts. For example, a user may decide to enable the oxygen saturation alert, set the alert to occur if and when the oxygen saturation level falls below a threshold value, and set the volume level of the alert.

The console may also include a mass storage device to store data. Examples of mass storage devices include mass disk drives, floppy disks, magnetic disks, fixed disks, hard disks, CD-ROM and CD-RW drives, DVD-ROM and DVD-RW drives, flash and other nonvolatile solid-state storage drives, tape storage, reader, and other similar devices, and combinations of these.

The stored data may include patient information. This includes, for example, the patient's name, social security number, or other identifying information, oxygen saturation measurements and the time and date measured. The oxygen saturation measurements may include high, low, and average values and elapsed time between measurements.

The above drives may also be used to update software in the console. The console may receive software updates via a communication network such as the Internet.

In an implementation, the console also includes an interface for transferring data to another device such as a computer. The interface may be a serial, parallel, universal serial bus (USB) port, RS-232 port, printer port, and the like. The interface may also be adapted for wireless transfer and download, such as an infrared port. The system transfers data without interruption in the monitoring of the patient.

Screen or display 310 on the console displays the patient's data. The screen may be a flat panel display such as a liquid crystal display (LCD), plasma display, thin film transistor liquid crystal display (TFT LCD), electroluminescent (EL), or organic light emitting diode (OLED) display. The screen may include a touch screen interface. Such touch screen interfaces are easier to clean compared to keypads if they become contaminated because they do not contain mechanical parts.

The screen may display numbers, text, graphics, and graphical trends in color. Different colors may correspond to different measurements or threshold levels. The text and numbers may be displayed in specific languages such as English, German, Spanish, French, Chinese, Japanese, or Tagalog. The displayed language is user-programmable.

In a specific implementation, the screen displays data related to a single regional oxygen saturation reading. For example, this may include a single plot or graph or two or more graphs to show oxygen saturation readings at different depths below the surface of the tissue.

Users can also vary the size of the displayed information on the console's display. This allows the display to be viewed at a distance, increases the viewing angle, and allows users with vision limitations to see the information.

In a specific implementation, the console includes one or more near-infrared radiation sources. In other implementations, the radiation sources are external to the console. For example, the radiation sources may be included within a separate unit between the console and probe or the radiation sources may be included on the probe. In another implementation, some radiation sources may be within the console while other radiation sources are external to the console.

Generally, these radiation sources are near-infrared lasers. In a specific implementation, there are four near-infrared lasers located within the console. In this specific implementation, two of laser sources emit radiation or light having a wavelength of about 690 nanometers and the other two laser sources emit radiation or light having a wavelength of about 830 nanometers.

In other implementations, there are less than four radiation sources or more than four radiation sources. For example, there may be 2, 3, 5, 6, 7, 8, 9, 10 or more than 10 radiation sources. These radiation sources generate approximately 100 milliwatts of power, but the power may range from about 70 milliwatts to about 130 milliwatts. For example, the power may be 75, 80, 85, 90, 95, 100, 105, 110, 115, 120, 125, or more than 130 milliwatts. Depending on the application, the power may be less than 75 milliwatts such as 30 milliwatts. Generally, the power generated by the radiation sources is sufficient so that light transmitted into the tissue and then reflected from the tissue is received by photodiodes in the probe or console such that the signal-to-noise ratio is greater than 10.

Figure 4:
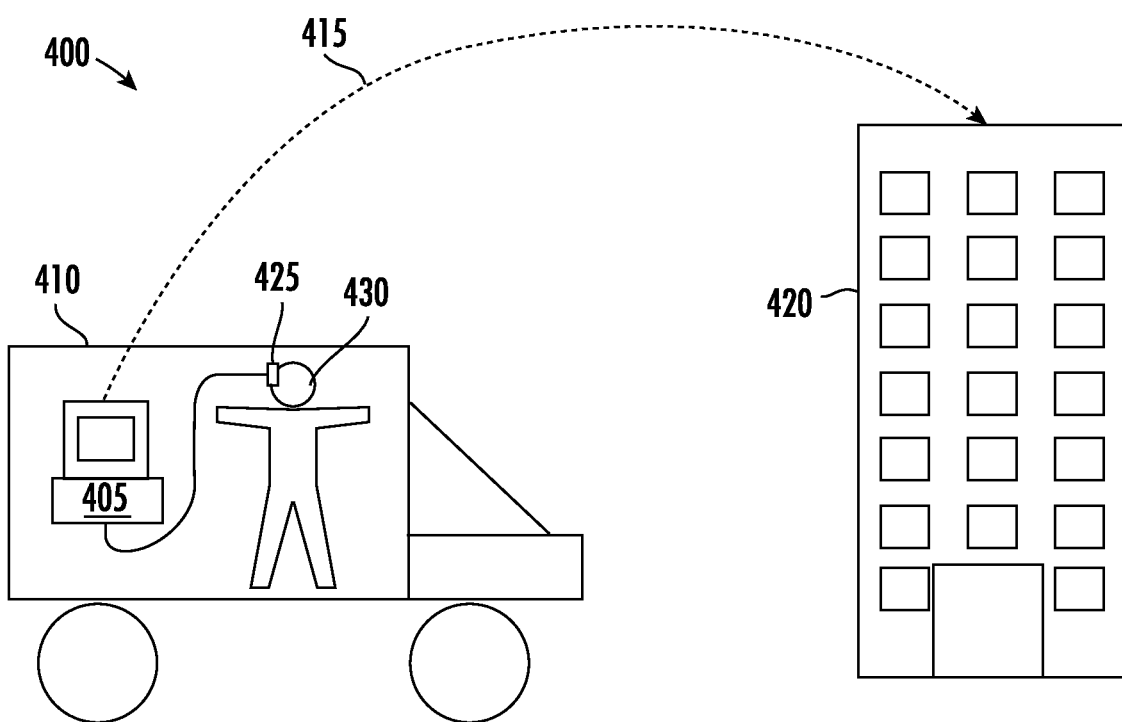
FIG. 4 shows a block diagram illustrating a wireless transmission of data from a field location to a receiving location.

FIG. 4 shows an example of a wireless implementation of the invention. A system 400 includes a monitoring console 405 at a field location 410 which transmits 415 the patient's data to a receiving location 420. The figure shows the monitoring console transmitting the data, using for example, a modem in the monitoring console. However, in another implementation, a probe 425 may wirelessly transmit the data to the receiving location.

In the figure, the field location is in an ambulance. The ambulance is transporting a patient 430 to a hospital. In other implementations, the field location may be in another type of vehicle such as a car, automobile, truck, bus, train, plane, boat, ship, submarine, or helicopter. The field location may also be on a battlefield, at an accident scene such as a car accident, at the scene of a natural disaster such as an earthquake, hurricane, fire, or flood, in a patient's home, at a patient's place of work, or in a nursing home.

The receiving location also varies. The receiving location may be a hospital, clinic, trauma center, physician's home or office, or a nurse's home or office. The monitoring console or probe may also transmit to multiple receiving locations. For example, data may be transmitted to both the hospital and the physician's home.

The data may be received by any variety of devices. Some examples of these receiving devices include a monitoring console, other monitoring stations, mobile devices (e.g., phones, smartphones, pagers, personal digital assistants (PDAs), laptops), or computers, or combinations of these.

The distance between the field and receiving location varies. The field and receiving location may be in different countries, states, cities, area codes, counties, or zip codes. The field location and receiving location may be in different parts of the same room or in different rooms in the same building.

The wireless transmission may be analog or digital. Although FIG. 4 shows the system transmitting data directly to the receiving location, this is not always the case. The system may relay data to the receiving location using intermediaries. For example, satellites may rebroadcast a transmission. While in one embodiment, a communication network is the Internet, in other embodiments, the communication network is any suitable communication network including a local area network (LAN), a wide area network (WAN), a wireless network, an intranet, a private network, a dedicated network, phone lines, cellular networks, a public network, a switched network, and combinations of these and the like. Wireless technologies that the system may employ include: Wi-Fi, 802.11a, 802.11b, 802.11g, 802.11n, or Bluetooth, or combinations of these and the like. The system also has the ability to switch from one communication technique to another if, for example, the current network is unreliable or there is interference. The switch may either be automatic or manual.

The system's ability to wirelessly transmit data offers several advantages. One advantage is that it reduces the time to treatment for a patient. For example, data sent from an ambulance en route to a hospital allows a physician at the hospital to mobilize personnel and equipment before the patient arrives. Another advantage is long-distance monitoring. For example, patients may use the system in their own homes. The system will then, on a continuous basis if desired, transmit data to a receiving location, such as a hospital. A nurse or physician at the hospital can then review the data. If the data indicates a problem with the patient, then the hospital can dispatch an ambulance to the patient's home.

Figure 5:
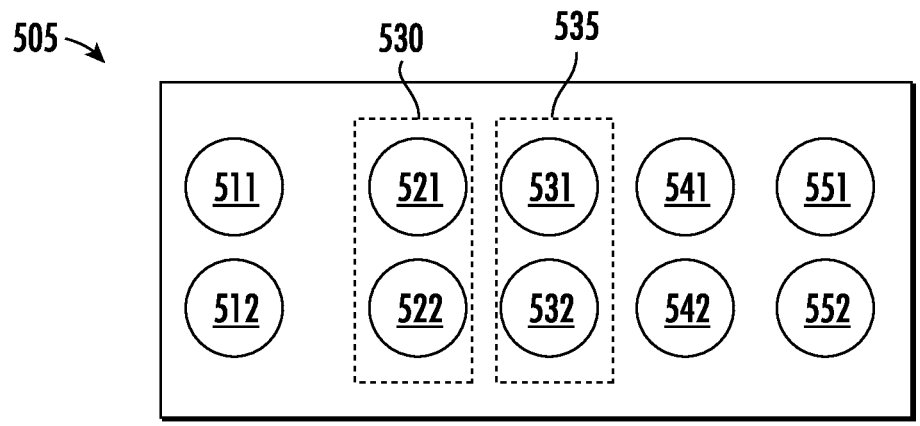
FIG. 5 shows an arrangement of sensor structures for a probe.

FIG. 5 shows an arrangement of sensor structures for a probe 505. This probe has 10 structures. Structures 511,521, 531,541, and 515 are in a first row, and structures 512,522, 532, 542, and 552 are in a second row. Each row has five columns. Structures 511-512 are in a first column. Structures 521-522 are in a second column. Structures 531-532 are in a third column. Structures 541-542 are in a fourth column. Structures 551-552 are in a fifth column. In other implementations, there can be any number of structures arranged in any number of desired rows and columns (e.g., two by three, two by four, three by four, or four by six).

This application describes the arrangement of sensors as an array of rows and columns, but as one of skill in the art will recognize, the entire array can be rotated ninety degrees, so that rows become columns and columns become rows.

Each of these columns has the same number of rows. Each of the rows has the same number of columns. However, in other implementations, a row may have a different number of structures than other rows. A column may have a different number of structures than other columns. For example, a first column may include two structures, while other columns include more than two structures (e.g., three or four structures).

In an implementation, the probe is for an oximeter device. In a first arrangement, structures 511-512 are source structures, and structures 521-522,531-532,541-542, and 551-552 are detector structures. In a second arrangement, structures 511 and 512 are detector structures, and structures 521-522,531-532,541-542, and 551-552 are source structures. In other implementations, any of the structures can be assigned as sources or detectors as desired.

The intensity of light emitted by the source structures may be the same or the intensity may vary. For example, in a specific implementation of the second arrangement, each pair of source structures 521-522,531-532,541-542, and 551-552 emits light at an intensity that is different from another pair of source structures. In this specific implementation, the intensity of light emitted by a pair of source structures increases with respect to the distance to detector structures 511-512. For example, the intensity of light emitted by source structures 551-552 is greater than the intensity of light emitted by source structures 541-542 since 551-552 are further away from detector structures 511-512 than 541-542. This helps to compensate for the attenuation of the light due to the distance between the source and detector structures. In another implementation, the intensity of light emitted by a pair of source structures decreases with respect to the distance to the detector structures.

In various implementations, each column (or row) is composed entirely of one type of structure, either source or detector, without other types of structures intervening. When a column (which may be along an edge of the array, or within the array) has structures of one type, the other structures in other columns are of another type. There can be any number of columns of a first type of structure, and any number of columns of a second type of structure, different from the first type. Also, there may be columns or rows of different types of structures intervening between the columns or rows of source and detector structures.

In FIG. 5, the structures shown are circular. However, in other implementations, the structures can have any shape, such as square, rectangle, hexagon, octagon, ellipse, any polygon shape, or any quadrilateral shape. In a specific implementation, each structure has the same cross-sectional area (e.g., same diameter). In another implementation, the cross-sectional area of one or more structures may be different from other structures. There can be any combination of differently sized structures.

Wires or cables may be connected to the structures. In particular, each of the structures may include a photodiode or other emitter device, a photodetector or other detector device, or fiber optic cable, in any combination.

For example, in implementation, in a first portion, structures 511-512 are sources with fiber optic cables. In a second portion, structures 521-522 and 531-532 are detectors with fiber optic cables. In a third portion, structures 541-542 and 551-552 are detectors with photodetectors (which are part of the probe). The second portion is between the first and the second.

Typically, the radiation or light received by detector structures further away from the source structures will be more attenuated than light received by detector structures closer to the source structures. Thus, for the detector structures positioned further away from the source structures, these detector structures (e.g., 541-542 and 551-552) may include photodetectors as part of the probe instead of transmitting a received signal through optical fiber to a photodetector at the console. By putting the photodetector in the probe, this prevents further attenuation of an already potentially weak signal by the optical fiber.

One benefit of using optical fiber instead of photodetectors is to reduce the cost of the probe because, typically, optical fiber is less expensive than photodetectors. Since the light received by detector structures nearer the sources will be less attenuated, optical fiber can be used at these detector structure positions (e.g., second portion of structures) and the measurements will still be accurate.

Thus, using an appropriate combination of optical fiber and photodiodes for the detector structures of a probe can help to minimize costs while facilitating accurate measurements. For example, a probe designed to measure not as deeply in the tissue can be made less expensively by not including photodetectors in the probe.

In other implementations, the second and third portions can be swapped. The numbers of structures in the second and third portions can be different from each other.

In a specific implementation, the sensor structures are on a plane of a probe face. The probe face may be rigid or formed of a flexible material which will adapt to the surface of the tissue the probe is being used to measure. Some examples of flexible materials include a foam, polymer, silicon, fabric, and rubber, and combinations of these. Sensors on flexible substrates are further discussed in U.S. patent application Ser. No. 12/326,491, filed Dec. 2, 2008, which is incorporated by reference along with all other references cited in this application.

Light shading or diffusing layers or films 530 and 535 may cover a portion of the sensors. Any number of sensors may be covered by one or both light shading films. For example, in FIG. 5, structures 521-522 and 531-532 are covered by light shading film 530 and 535, respectively, while 541-542 and 551-552 are not.

Although FIG. 5 shows two light shading films there can be any number of light shading films (e.g., one, two, or three light shading films). For example, light shading films 530 and 535 can be combined into one light shading film. The light shading films are optional and some implementations do not include the light shading films. In an implementation, a column has structures of a first type (e.g., along an edge of the array), and the other structures in other columns are of a second type; the light shading film is applied to one or more columns of the second type. These columns covered by the light shading film may be adjacent columns or nonadjacent columns (in which cases there can be two or more separate pieces or films).

Further, there may be different types of light shading films having different transmission or filtering characteristics or coefficients. Two or more light shading films may be placed on top of each other to obtain one or more desired shading or light transmission characteristics.

In a specific implementation, a first column has structures of a first type (e.g., source structures), and second and third columns have structures of a second type (e.g., detector structures). The first column is closer to the second column than the third column. A first light shading film allows a first percentage of light (or first type of filtering) to pass through. A second light shading film allows a second percentage of light (or second type of filtering) to pass through. The first light shading film is darker than the second light shading film (i.e., the first percentage is less than the second percentage). The first light shading film covers the second column while the third column is uncovered or exposed or covered by the second light shading film. In another implementation, the first or second light shading film is applied to the third column and the second column is uncovered. The second and third columns can be adjacent columns or may be separated by another column (e.g., one or more columns of structures of the second type).

In an implementation of the first arrangement where 511-512 are source structures and 521-522,531-532,541-542, and 551-552 are detector structures, the light shading film closer to the source structures (i.e., light shading film 530) is darker than the light shading film further away from the source structures (i.e., light shading film 535). Light shading film 535 allows a greater percentage of light to pass through than light shading film 530. For example, light shading film 530 may have a higher optical density than light shading film 535. It should also be appreciated that a single light shading film may have two or more regions with different optical properties. For example, a portion of the single light shading film can have a different optical density than another portion of the single light shading film.

In various other implementations, two or more light shading films allow the same percentage of light to pass through. A light shading film that is further away from the source structures is darker or has a higher optical density than another light shading film closer to the source structures.

Typically, the light shading film is a semitranslucent film or filter, but it may also be a screen (e.g., perforated screen), or a coating that may be painted or sprayed onto structures of a particular type. For example, the light shading film can be a gray or dark film to reduce, attenuate, shield or partially shield, partially block, or partially shade light arriving at a photodiode or photodetector.

In a specific implementation, the light shading film is an optical filter. Some examples of optical filters include absorptive filters which absorb some wavelengths of light while transmitting other wavelengths of light, interference or dichroic filters which reflect some wavelengths of light while transmitting other wavelengths of light, monochromatic filters, infrared filters, ultraviolet filters, neutral density filters, longpass filters, shortpass filters, bandpass filters, polarization filters, and colored filters.

In a specific implementation, the second column of detectors 521 and 522 is covered by a first spectral filter 530 and the third column of detectors 531 and 532 is covered by a second spectral filter 535. The second column of detectors is closer to the first column of sources 511 and 512 than the third column. As discussed, in an implementation, the first and second spectral filters are different. For example, the first spectral filter may allow in less light intensity to pass though to the detectors than the second spectral filter. This arrangement of spectral filters is to reduce reflections received at the second column. Since the second column is closer to the first, more reflections may result. There can be more than two filters arranged in decreasing attenuation (or transmittance) as the distance increases from the sources.

In an alternate implementation, however, the first spectral filter allows more light intensity to pass than the second spectral filter. This arrangement may be useful depending on the tissue or part of a body being measured. For example, there may be bone or other more highly reflective tissue that is closer to the probe surface further away from the sources.

Further, the first spectral filter may allow in a different spectrum of light to pass though to the detectors than the second spectral filter. For example, the first spectral filter may attenuate certain wavelengths of light (e.g., blue light, green light, or specific wavelengths 470-490 nanometers) at higher attenuation levels than the second spectral filter. But other wavelengths (e.g., other than 470-490 nanometers) would pass through the first and second spectral filters at the same attenuation level.

Such optical filters can have any optical density. Typically, the optical density of an optical filter used in various implementations of a probe ranges from about 0.30 (which transmits about 50 percent of visible light) to an optical density of about 1.2 (which transmits about 6.25 percent of visible light). Two or more optical filters may be combined to produce a desired optical density. Generally, optical densities are additive. For example, combining an optical filter having an optical density of 0.30 with an optical filter having an optical density of 0.90 results in a combined optical density of 1.20.

The light shading film may be made of plastic, nylon, crystallized polymers (e.g., polypropylene or polyethylene), polyethylene terephthalate (PET), metal, cloth, textile (e.g., nonwoven fabric and woven fabric) or glass. In a specific embodiment, the film absorbs about 90 percent of light at the wavelengths used in a typical implementation of the invention. However, the amount of light absorbed may range from about 60 percent to about 99 percent. In some implementations, the amount of light absorbed is less than 60 percent.

The light shading film generally helps to minimize, reduce, or attenuate undesirable optical effects. Undesirable optical effects may include light that is back reflected from shallow tissue layers (e.g., scalp, skull, and cerebrospinal fluid). In a specific implementation, the film helps to insure that the signal level received by the detector structures covered by the film is within the dynamical range or sensitivity of the photodiodes or other photodetecting device. The light shading film may cover or be placed over detector structures that include photodiodioes, optical fiber, or both.

The above discussion describes using physical or optical filters at the probe. In other implementations, however, spectral filtering may be done using digital, analog, electronic, or computerized filtering techniques. For example, a user may tailor a spectrum using an equalizer function (e.g., through a histogram or spectral display) available at the console. The same or similar type of filtering available through physical filtering may be performed by using software at the console. A physical filter may however be able to filter out noise or unwanted characteristics before they reach the console.

A distance between the first and second columns is less than a distance between the first and third columns. Distance can be measured from a reference point for each column. For example, this reference point can be a point on a line connecting structures of a particular column. For example, the reference points may be the centers of structures 511, 521, and 531.

A distance between the first column and the second column can be greater than the distance between the second and third column. In other implementations, this distance can be the same or different (e.g., less). In an implementation, the first column has structures of a first type (e.g., source or detector), while the second and third columns have structures of a second type, different from the first.

Distances between the second, third, fourth, and fifth columns can be the same, or may vary. In other words, the columns, rows, or both may or may not be equally spaced or distributed on a face of a probe. In various implementations there are at least three or more rows equally spaced (e.g., four rows equally spaced), at least three or more columns equally spaced (e.g., four columns equally spaced), or both. Typically, when the at least three or more rows are equally spaced the distance between adjacent rows of the at least three or more rows is equal to the distance between the first and last row divided by the number of rows minus one. Similarly, when the at least three or more columns are equally spaced the distance between adjacent columns of the at least three or more columns is equal to the distance between the first and last columns divided by the number of columns minus one.

Thus, a distance between a pair of columns may be the same as or different from a distance between another pair of columns. In an implementation, a first distance between a column having structures of a first type and another column having structures of a second type is different from a second distance between a pair of columns having structures of the same type. In this specific implementation, the first distance is greater than the second distance. In another implementation, the second distance is greater than the first distance.

In specific implementations, the distance between columns ranges from about 5 millimeters to about 80 millimeters. For example, the distance between two adjacent columns may be about 10, 15, 20, 25, 30, 35, 40, 45, 50, 55, 60, 70, or 79 millimeters. Depending upon the application, the distance may be less than 5 millimeters or greater than 80 millimeters.

In various implementations, at least three structures in a column (or row) are each positioned on the same line or at least one structure of the at least three structures is positioned on a different line. When the structures are positioned on the same line, one line can pass through a reference point of the at least three structures. The reference point may be defined as the centers of the structures if, for example, the structures have circular shapes. The reference point may be defined as some other point, so long as the definition is consistent among the structures. When the at least one structure is positioned on a different line, two or more lines are needed to pass through reference points of the at least three structures.

A line passing through the reference points of the structures in a column (or row) may be parallel to or intersect (i.e., not parallel to) a line passing through the reference points of the structures in another column (or another row). In a specific embodiment, a first line passing through the reference points of structures of a first type in a first column intersects or is not parallel to a second line passing through the reference points of structures of a second type in a second column. In another embodiment, the first and second lines are parallel.

In an implementation, structures 511-512 are arranged in a first line, where this line is parallel to the lines of structures 521-522,531-532,541-542, and 551-552. In another implementation, the first line intersects (or is not parallel with) at least one of the lines through structures 521-522,531-532, 541-542, or 551-552.

The probe is typically connected to the console via a cable. The cable may attach to the probe at any edge or surface of the probe. Typically, the cable attaches to the probe via a surface that is different from the surface which the structures are on. For example, the cable can attach to the probe via a side surface or back surface (opposite a front face, which has the structures).

In a specific implementation, the cable attaches at an edge of the probe that is furthest away from structures 511-512. In another implementation, the cable attaches at an edge that is furthest away from structures in the first row (511, 521, 531, 541, and 551).

FIGS. 12-19 show specific implementations of a probe of FIG. 5.

FIGS. 6-11 show various specific implementations of arrangements for sensor structures of a probe. Any of these implementations may be used in conjunction with any of the implementations discussed in this application. The sensor structures can be either source structures or detector structures. Although specific numbers of sensors are shown, the arrangements can be expanded to have more sensors per column or more sensors per row, or both.

Figure 6:
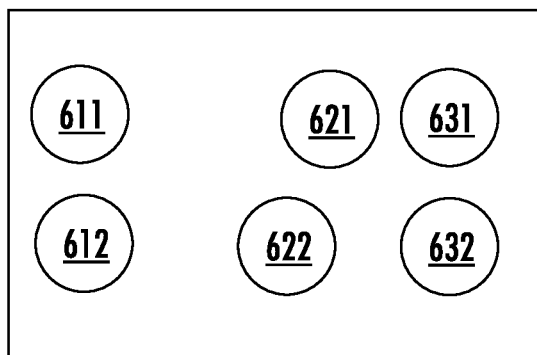
FIG. 6 shows a sensor opening pattern where one sensor opening is aligned asymmetrically with respect to the other sensor openings.

FIG. 6 shows a specific implementation of a probe. Structures 621-622 are aligned differently than sensors 611-612 and 631-632. That is, at least one structure in the column (i.e., structure 621) is positioned asymmetrically. In particular, a line drawn through reference points of structures in the second column (621-622) is not parallel to a line drawn through reference points of structures in the first column (611-612) or the third column (631-632). A line drawn through the first row (611, 621, and 631) is parallel to a line drawn through the second row (612, 622, and 632).

A first distance between structures 611 and 622 does not equal a second distance between structures 612 and 621. The distance between structures 611 and 632 equals the distance between structures 612 and 631.

The asymmetrical positioning allows tissue oxygenation measurements of a nonuniform or inhomogeneous volume of tissue. For example, the probe may be positioned over a tissue volume which includes bone, muscle, blood vessels, fascia, and nerves. Light may be absorbed by regions that are unusually absorptive or be reflected off of structures such as bone—which may result in incorrect measurements. In other words, the distribution of capillaries containing oxygenated hemoglobin in this tissue volume is not uniform. However, the asymmetric orientation of source structures, detector structures, or both on a probe helps to facilitate the transmission and receipt of light that avoids regions in the tissue volume, such as bone, that may result in incorrect measurements. Asymmetrical positioning is further discussed in U.S. Pat. No. 7,355,688, issued Apr. 8,2008, which is incorporated by reference along with all other references cited in this application. Further, a beam combiner may be included in the console as discussed in the '688 patent.

In an implementation, structures 611-612 are sources while 621-622 and 631-632 are detectors. In another implementation, structures 611-612 are detectors while 621-622 and 631-632 are sources. In various other implementations, 621-622 are a first type of sensor while 611-612 and 631-631 are a second type of sensor, different from the first.

In FIG. 6, one column is aligned asymmetrically with respect to the first column. However, in other implementations, any number of columns can be aligned asymmetrically with respect to the first column (e.g., two, three, four, or more than four). For example, 621-622 and 631-632 are aligned asymmetrically with respect to 611-612.

Figure 7:
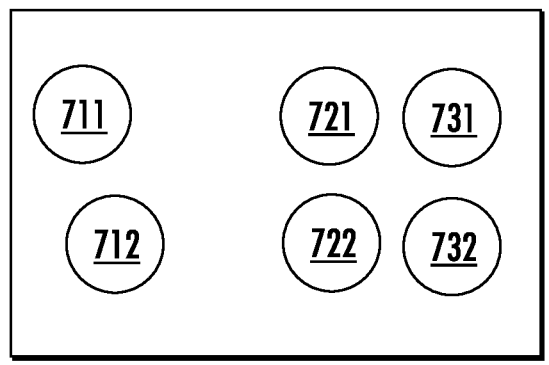
FIG. 7 shows another sensor opening pattern where one sensor opening is aligned asymmetrically with respect to the other sensor openings.

FIG. 7 shows another asymmetrical position arrangement for a probe. In this probe a structure 712 in the first column is aligned differently than structures in the second column (721-722) and third column (731-732). In an implementation, the first column is between an edge of the probe and the second column.

Similar to FIG. 6, a first distance between structures 711 and 722 does not equal a second distance between structures 712 and 721. However, unlike FIG. 6, the distance between structures 711 and 732 does not equal the distance between structures 712 and 731.

In an implementation, structures 711-712 are sources while 721-722 and 731-732 are detectors. In another implementation, structures 711-712 are detectors while 721-722 and 731-732 are sources. In various other implementations, 721-722 are a first type of sensor while 711-712 and 731-732 are a second type of sensor, different from the first. Sensors 731-732 are a first type of sensor while 711-712 and 721-722 are a second type of sensor, different from the first.

In FIG. 7, column 711-712 is aligned asymmetrically with respect to the other columns. However, in other implementations, any number of columns can be aligned asymmetrically with respect to this column (e.g., one, two, three, four, or more than four). For example, 711-712 and 721-722 are aligned asymmetrically with respect to 731-732. Sensors 711-712 and 721-722 can be parallel to each other.

Figure 8:
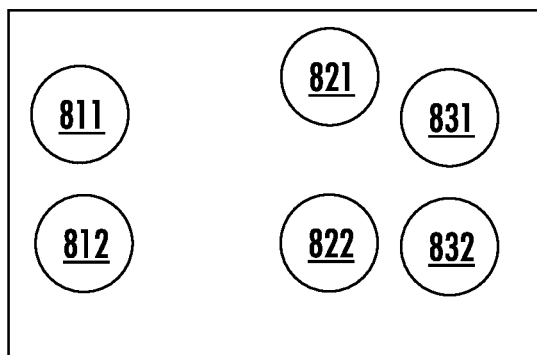
FIG. 8 shows another sensor opening pattern where one sensor opening is aligned asymmetrically with respect to the other sensor openings.

FIG. 8 shows another asymmetrical position arrangement for a probe. The probe in this specific implementation includes a structure 821 in the second column that is aligned with another structure 822 in the second column. This is in contrast to FIG. 6 where structure 621 is not aligned with 622. However, in this probe, structure 821 is still aligned differently with respect to structures in the first column (811-812) and third column (831-832).

A straight line drawn through reference points of structures 811 and 831 does not pass through the reference point of structure 821. Rather, the reference point of structure 821 is above the straight line. In another implementation, the reference point of structure 821 is below the straight line.

Column 821-822 is asymmetrical with respect to the other columns in FIG. 8. This is similar to the arrangement of columns 621-622 in FIG. 6. However, in this probe, structure 821 is asymmetrical, offset, or skewed in a vertical direction whereas structure 621 in FIG. 6 is offset in a horizontal direction.

Similar to FIG. 6, a first distance between structures 811 and 822 does not equal a second distance between structures 812 and 821. The distance between structures 811 and 832 equals the distance between structures 812 and 831.

In further implementations of the invention (not shown) a sensor can be positioned asymmetrically with respect to both its row and column. That is, the sensor can be offset in both a horizontal direction—structure 621 (FIG. 6)—and a vertical direction—structure 821 (FIG. 8). A line drawn through reference points of other structures in the column that includes this asymmetrical sensor does not pass through the reference point of the asymmetrical sensor. Similarly, a line drawn through reference points of other structures in the row does not pass through the reference point of the asymmetrical sensor. There can be any number of such asymmetrical sensors and they can be positioned in any column (e.g., first, second, or third column) or any row (e.g., first, second, or third row). Further discussion on asymmetrical sensors is provided in U.S. Pat. No. 7,355,688, issued Apr. 8,2008, which is incorporated by reference.

In an implementation, structures 811-812 are sources while 821-822 and 831-832 are detectors. In another implementation, structures 811-812 are detectors while 821-822 and 831-832 are sources. In various other implementations, 821-822 are a first type of sensor while 811-812 and 831-832 are a second type of sensor, different from the first. Sensors 831-832 are a first type of sensor while 811-812 and 821-822 are a second type of sensor, different from the first.

Figure 9:
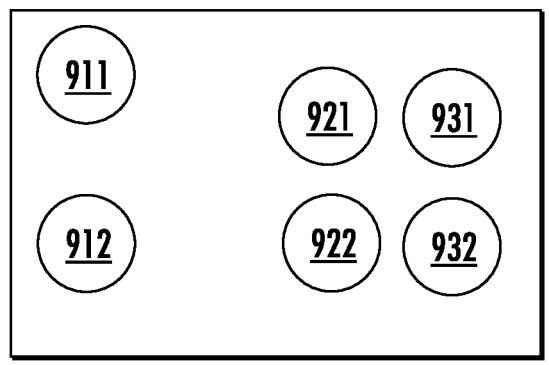
FIG. 9 shows another sensor opening pattern where one sensor opening is aligned asymmetrically with respect to the other sensor openings.

FIG. 9 shows another asymmetrical position arrangement for a probe. This arrangement is a variation of the arrangement shown in FIG. 8. In this probe a structure 911 in the first column is aligned with another structure 912 in the first column, but is aligned differently with respect to structures in the second column (921-922) and third column (931-932).

Similar to FIG. 8, a first distance between structures 911 and 922 does not equal a second distance between structures 912 and 921. However, in contrast to FIG. 8, the distance between structures 911 and 932 does not equal a distance between structures 912 and 931.

In an implementation, structures 911-912 are sources while 921-922 and 931-932 are detectors. In another implementation, structures 911-912 are detectors while 921-922 and 931-932 are sources. In various other implementations, 921-922 are a first type of sensor while 911-912 and 931-932 are a second type of sensor, different from the first. Sensors 931-932 are a first type of sensor while 911-912 and 921-922 are a second type of sensor, different from the first.

Figure 10:
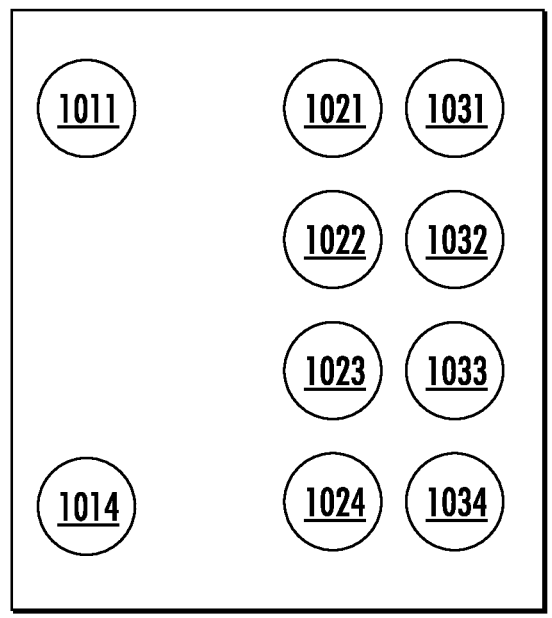
FIG. 10 shows another sensor opening pattern where one column has a different number of sensor openings with respect to other columns.

FIG. 10 shows another asymmetrical probe where the asymmetry includes columns with different numbers of structures. In particular, this probe includes a first column that includes a different number of structures than the second and third columns. The first column includes two structures 1011 and 1014. The second column includes five structures (1021-1024). The third column also includes five structures (1031-1034).

Structures 1011 and 1014 are each positioned at ends of the first column. However, in other implementations, structures 1011 and 1014 may be positioned anywhere within the first column.

In an implementation, structures 1011 and 1014 are source structures while 1021-1024 and 1031-1034 are detectors. In another implementation, structures 1011 and 1014 are detectors while 1021-1024 and 1031-1034 are sources.

In various other implementations, structures 1021-1024 are a first type of sensor while 1011 and 1014 and 1031-1034 are a second type of sensor, different from the first. Sensors 1031-1034 area first type of sensor while 1011 and 1014 and 1021-1024 area second type of sensor, different from the first. At least one column has a different number of structures than another column; at least two columns have the same number of structures. An implementation can include some columns having the same number of structures and other columns having a different number of structures. For example, a probe may include three columns having the same number of structures (e.g., two source structures) and one column having a different number of structures (e.g., four detector structures).

Figure 11:
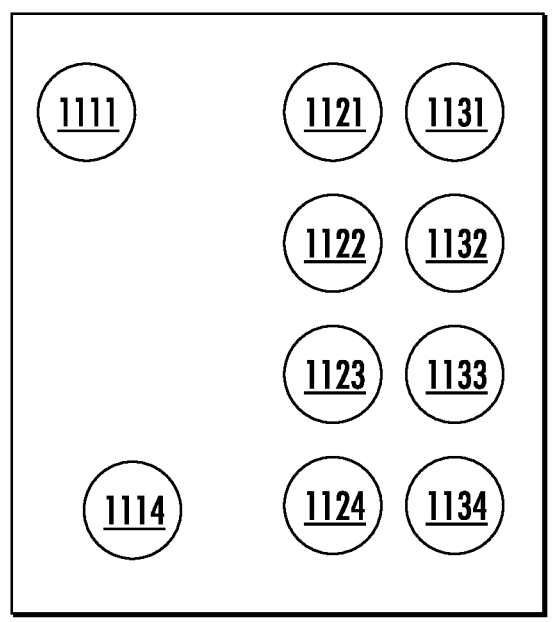
FIG. 11 shows another sensor opening pattern where one column has a different number of sensor openings and a sensor opening that is aligned asymmetrically with respect to other columns.

FIG. 11 shows another asymmetrical position arrangement for a probe. This probe is a variation of the probe shown in FIG. 10. Structures 1111 and 1114 in the first column are aligned differently than structures in the second column (1121-1124) and structures in the third column (1131-1134).

Similar to FIG. 10, structures 1111 and 1114 are each positioned at ends of the first column, but can be positioned anywhere within the first column. For example, a structure such as structure 1111 may be positioned in the second or third row. Structure 1111 may also be offset in a horizontal direction, offset in a vertical direction (see structure 911, FIG. 9), or offset in both a horizontal and vertical direction.

A distance between structures 1111 and 1124 does not equal a distance between structures 1114 and 1121. A distance between structures 1111 and 1122 does not equal a distance between structures 1114 and 1123. A distance between structures 1111 and 1134 does not equal a distance between structures 1114 and 1131. A distance between structures 1111 and 1132 does not equal a distance between structures 1114 and 1133.

In an implementation, structures 1111 and 1114 are source structures while 1121-1124 and 1131-1134 are detectors. In another implementation, structures 1111 and 1114 are detectors while 1121-1124 and 1131-1134 are sources. In various other implementations, structures 1121-1124 area first type of sensor while 1111 and 1114 and 1131-1134 area second type of sensor, different from the first. Sensors 1131-1134 are a first type of sensor while 1111 and 1114 and 1121-1124 are a second type of sensor, different from the first.

Sensor opening patterns are further discussed in U.S. patent application Ser. No. 11/963,069, filed Dec. 21, 2007; and U.S. patent application Ser. No. 12/178,359, filed Jul. 23, 2008, which are incorporated by reference along with all other references cited in this application.

Figure 12:
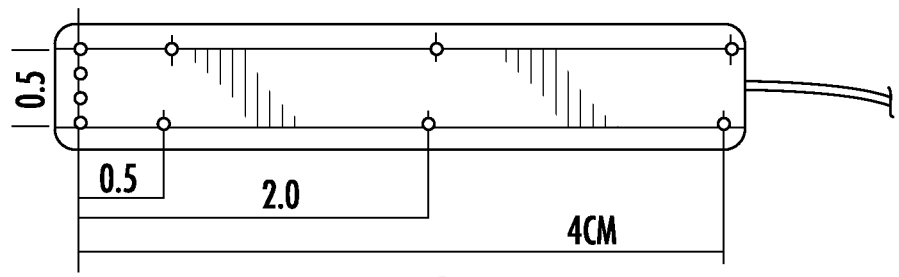
FIG. 12 shows a specific embodiment of a probe with one column of four detectors and three columns of source pairs.

FIGS. 12-19 show various specific implementations of a probe of FIG. 5. These probes have fixed sensor positions. In FIG. 12, the probe has a first column including four detector structures, a second column including two source structures, a third column including two source structures, and a fourth column including two source structures. All source structures are on the same side (i.e., to the right) of the detector structures.

A fiber optic cable connects to the probe though an edge (i.e., right edge) that is furthest away from the first column. The ends of optical fibers connect to (or form the) the source and detector structures of the probe.

The source structure columns are in an asymmetrical or offset arrangement with respect to the detector structure column. For example, a first line passing through reference points of the first column of detector structures is not parallel to (or intersects with) (i) a second line passing through reference points of the second column of source structures; (ii) a third line passing through reference points of the third column of source structures; or (iii) a fourth line passing through reference points of the fourth column of source structures.

As shown, a distance between the first and second column is about 0.5 centimeters. A distance between the first and third column is about 2 centimeters. A distance between the first and fourth column is about 4 centimeters. A distance (or width) between a top row and bottom row of sensors is about 0.5 centimeters.

Using the three pairs of sources, one can use this probe to make tissue oxygen saturation measurements at depths of about 0.5, 2, and 4 centimeters below the surface of the tissue. See FIGS. 24-25 and accompanying discussion for further details on making tissue oxygen saturation measurements at different depths.

In a specific implementation, a pair of sources emits light at an intensity different from another pair of sources. The second column of source structures emits light at a first intensity. The third column of source structures emits light at a second intensity. The fourth column of source structures emits light at a third intensity. The third intensity is greater than the second and first intensities. The second intensity is greater than the first intensity. In various other implementations, the first, second, and third intensities are the same. The first intensity is greater than the second and third intensity. The second intensity is greater than the third intensity. Two or more intensities are the same. Two or more intensities are different.

As was discussed for FIG. 5 above, there are many variations of a probe of FIG. 12. For example, other implementations can include less than four detector structures such as one, two, or three detector structures. The sources can be to the left of the detectors, instead of the right. Various other implementations include one column having any number detector structures (e.g., two, three, or four detector structures) and two or more pairs of source structures (e.g., three, four, or five pairs of source structures); or one column having any number of source structures (e.g., two, three, or four source structures) and two or more pairs of detector structures (e.g., three, four, or five pairs of detector structures). Some examples of these implementations are shown in the probes of FIGS. 13-19.

Figure 13:
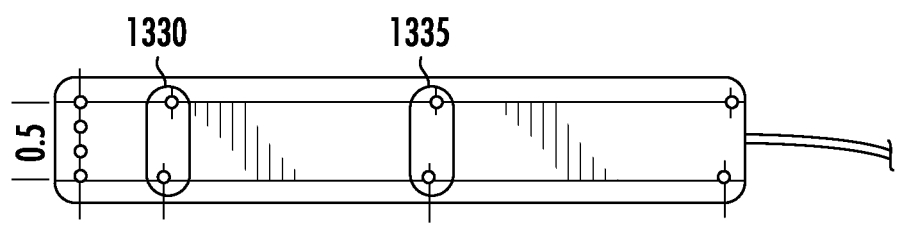
FIG. 13 shows a specific embodiment of a probe where the sources and detectors of the probe in FIG. 12 are swapped.

FIG. 13 shows a variation of the implementation of the probe shown in FIG. 12. As compared to the probe shown in FIG. 12, the source and detector structures are swapped and light shading films are included. A first light shading film 1330 covers a second column of two detector structures. A second light shading film 1335 covers a third column of two detector structures. A fourth column of two detector structures is not covered by a light shading film. The first light shading film is darker than the second light shading film.

Figure 14:
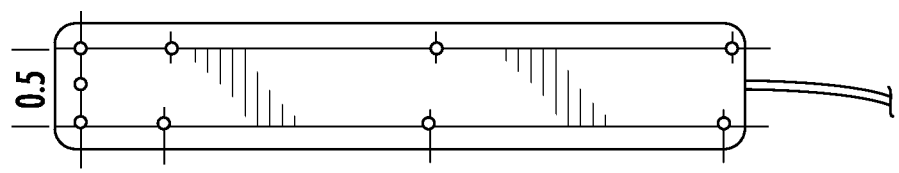
FIG. 14 shows a specific embodiment of a probe with one column of three detectors and three columns of source pairs.

FIG. 14 shows another variation of the implementation of the probe shown in FIG. 12. This probe has a first column including three detector structures and second, third, and fourth columns that each include two source structures.

Figure 15:
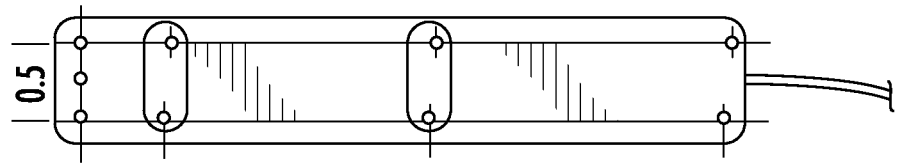
FIG. 15 shows a specific embodiment of a probe where the sources and detectors of the probe of FIG. 14 are swapped.

FIG. 15 shows a variation of the implementation of the probe shown in FIG. 14. As compared to the probe shown in FIG. 14, the source and detector structures are swapped and light shading films are included. A first light shading film covers a second column of two detector structures. A second light shading film covers a third column of two detector structures. A fourth column of detector structures is not covered by a light shading film. The first light shading film is darker than the second light shading film.

Figure 16:
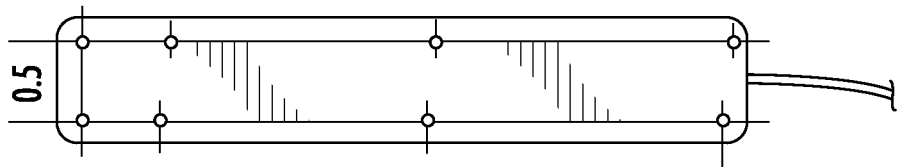
FIG. 16 shows a specific embodiment of a probe with one column of two detectors and three columns of source pairs.

FIG. 16 shows another variation of the implementation of the probe shown in FIG. 12. This probe has a first column including two detector structures and second, third, and fourth columns that each include two source structures.

Figure 17:
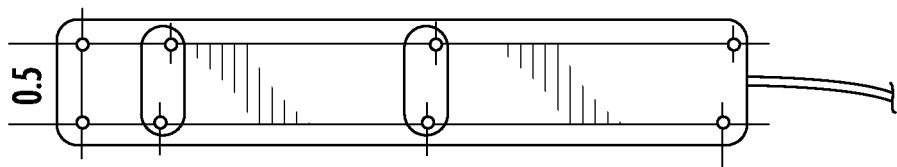
FIG. 17 shows a specific embodiment of a probe where the sources and detectors of the probe of FIG. 16 are swapped.

FIG. 17 shows a variation of the implementation of the probe shown in FIG. 16. As compared to the probe shown in FIG. 16, the source and detector structures are swapped and light shading films are included. A first light shading film covers a second column of two detector structures. A second light shading film covers a third column of two detector structures. A fourth column of detector structures is not covered by a light shading film. The first light shading film is darker than the second light shading film.

Figure 18:
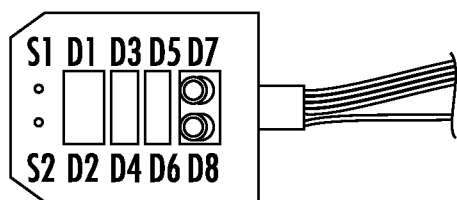
FIG. 18 shows another embodiment of a probe with one column of sources and four columns of detectors where a light shading film covers the column of detectors nearer to the column of sources.

FIG. 18 shows another embodiment of a probe with fixed sensor positions. The probe has a first column including two source structures (S1 and S2), a second column including two detector structures (D1 and D2), a third column including two detector structures (D3 and D4), a fourth column including two detector structures (D5 and D6), and a fifth column including two detector structures (D7 and D8). All detector structures are on the same side (i.e., to the right) of the source structures.

The source structures include apertures including optical fiber ends, which are connected to an optical fiber cable. The detector structures include photodetectors or photodiodes, which are connected to an electrical cable. The optical fiber cable connects the source structures to laser diodes within or inside the console. The electrical cable connects the photodetectors to the console.

The source structure column is in an asymmetrical or offset arrangement with respect to the detector structure columns. For example, a first line passing through reference points of the first column of source structures is not parallel to (or intersects with) (i) a second line passing through reference points of the second column of detector structures; (ii) a third line passing through reference points of the third column of detector structures; (iii) a fourth line passing through reference points of the fourth column of detector structures; or (iv) a fifth line passing through reference points of the fifth column of detector structures.

A first light shading film covers detector structures D1 and D2. A second light shading film covers D3 and D4. A third light shading film covers and D5 and D6. Detectors D1-D6 are closer to the source structures than detector structures D7 and D8. Detector structures D7 and D8 are exposed or open to the air.

As was discussed for FIG. 5 above, there are many variations of a probe of FIG. 18.

Figure 19:
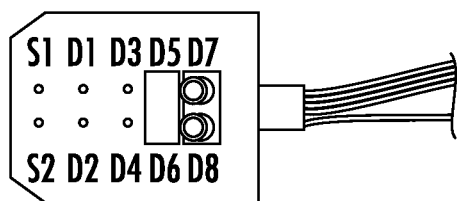
FIG. 19 shows another embodiment of a probe where two columns of detectors with optical fiber are between a column of sources and two other columns of detectors with photo-detectors.

FIG. 19 shows another embodiment of a probe with fixed sensor positions. This probe is similar to the probe in FIG. 18. But, in this probe the second column of detector structures (D1 and D2) and the third column of detector structures (D3 and D4) include the ends of optical fibers instead of the photodetectors as in FIG. 18. The optical fibers connect detector structures D1 and D2, and D3 and D4 to photodetectors inside the console. These detector structures are closer to the source structures as compared to detector structures D5 and D6, and D7 and D8, which include photodetectors at the probe.

Similar to the probe of FIG. 18, a light shading film covers detector structures D5 and D6 which are closer to the source structures as compared detector structures D7 and D8. However, a light shading film does not cover detector structures D1 and D2, and D3 and D4 which include optical fiber (e.g., within or held by an aperture).

As was discussed for FIG. 5 above, there are many variations of a probe of FIG. 19.

Figure 20:
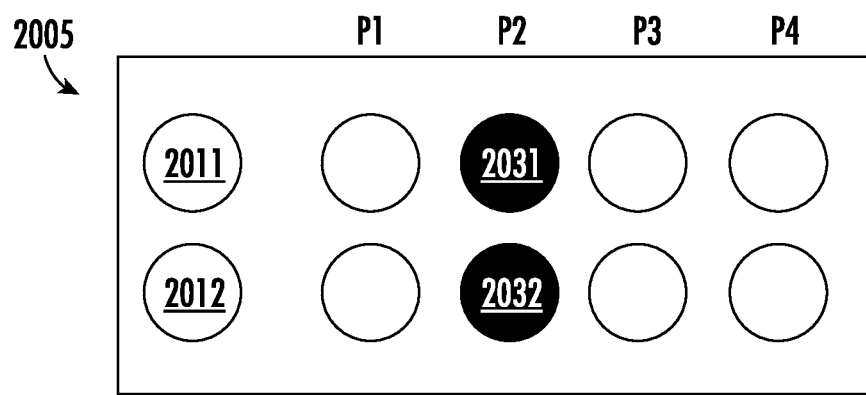
FIG. 20 shows a probe with empty openings in which a user can vary the distance between sources and detectors by inserting a source or detector into an empty opening.

FIG. 20 shows an arrangement of sensor structures for a probe 2005. Probe 2005 is similar to probe 505 described above and shown in FIG. 5. However, structures in columns P1, P2, P3, and P4 are for holding a source or detector. These structures may be openings or holes that can accept or receive structure connectors. For example, FIG. 20 shows structures 2031-2032 occupying openings in column P2 (i.e., indicated by solid black fill). A user can remove structures 2031-2032 and move them to any of the open (or unfilled) columns in order to vary a distance between structures 2011-2012.

In a specific implementation, structures 2011-2012 are source structures and structures 2031-2032 are detector structures. In another implementation, structures 2011-2012 are detectors while structures 2031-2032 are sources.

Figure 21:
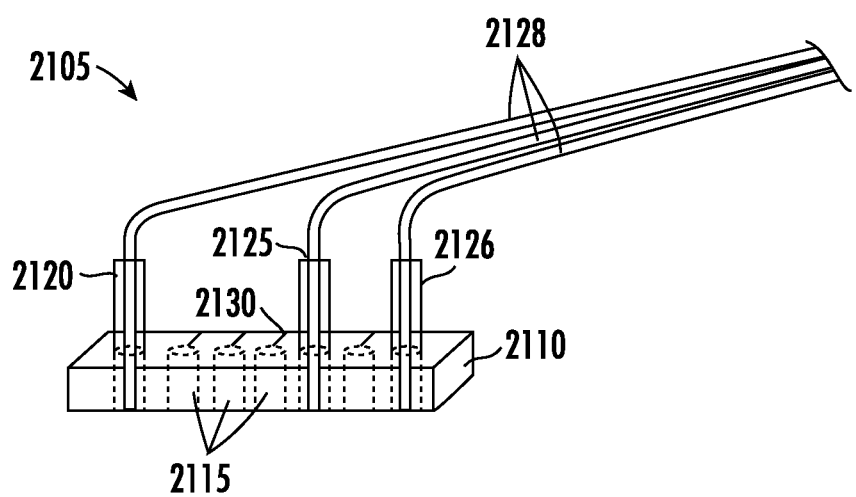
FIG. 21 shows a specific embodiment of a probe with moveable sensors.

FIG. 20 shows a pair of movable structures 2031-2032, but in other implementations, there can be any number of movable structures (e.g., more than two). Further, structures 2011-2012 can also be movable, in a similar way as structures 2031-2032. However, some of the structures can be fixed. For example, 2011-2012 can be fixed, while 2031-2032 are movable. Structures 2031-2032 can be fixed, while 2011-2012 are movable. FIG. 21 shows a specific implementation of the probe of FIG. 20.

Generally, the distance between a source and detector is used to calculate the tissue oxygenation for a tissue layer. (see FIG. 25 and accompanying discussion for further details). Thus, probe 2005 can include a mechanism for electronically detecting which of the holes is holding a sensor (e.g., detector or source). This information can then be used by the console to calculate the tissue oxygenation for a tissue layer. In a specific implementation, each hole in columns P1-P4 includes an electric switch. When a sensor is in a hole, the switch is closed or enabled. When a hole is empty, the switch is opened or disabled.

In another implementation, a probe includes a set of markings adjacent to the holes that indicate the source and detector separation. In this specific implementation, the user can use the set of markings to indicate to the console the source and detector separation or the position of a source or detector. See FIG. 21 and accompanying discussion.

A light shading film as shown in FIG. 5 and discussed above may be placed over any of the structures of probe 2005. For example, a portion of the light shading film may include a strip of adhesive material (e.g., pressure sensitive adhesive). The user can remove a release liner covering the adhesive strip and press the light shading film onto the bottom surface of the probe to cover any desired structure.

FIG. 21 shows a specific embodiment of the probe shown in FIG. 20. A probe 2105 includes a panel 2110 including a set of structures 2115 with openings for holding one source or one detector. This probe includes a source 2120 and two detectors 2125 and 2126 positioned lengthwise along the panel. Cables 2128 are connected to the source and detectors. A set of markings 2130 is adjacent to the openings.

The set of markings may include lines, graduated lines, numbers, characters, symbols, letters, text, colors, graphics, or combinations of these. Such markings may be made using any technique for making a visible impression on the probe including, but not limited to, printing, silkscreen printing, masking, stamping, plating, thermography, embossing, painting, engraving, etching, anodizing, oxidizing, deposition, imprinting, and chemical processing.

In a specific embodiment, the set of markings correspond to one or more units of measurement (e.g., millimeters, centimeters, and inches). The set of markings allow the user to determine the distance between sensors without having to use a separate ruler or measuring tape to measure the distance.

In another embodiment, the set markings correspond to controls (e.g., buttons) on the console that the user selects to indicate to the system the position of the sensors on the probe.

For example, a first marking (e.g., green marking) adjacent to a first opening may correspond to a first button (e.g., green button) on the console. A second marking (e.g., blue marking) adjacent to a second opening may correspond to a second button (e.g., blue button) on the console. If the user inserts a sensor into the first opening on the probe then the user will indicate the position of the sensor to the system by pressing the first button. Conversely, if the user inserts the sensor into the second opening then the user will press the second button. This position information is then used by the system in making tissue oxygen saturation measurements. See FIG. 25 and accompanying discussion for further details.

The sensors can be removably connected to the openings using any means. Generally, the sensors are fit into the openings using a press or interference fit. Friction between the sensor and the opening prevents the sensor from accidentally falling or slipping out. However, in another embodiment, the sensors are threaded into the openings. The sensors include first thread teeth that engage with second thread teeth in the openings. Other examples of removably connecting the sensors to the openings include snap fits and lug closures (e.g., insert sensor into opening and twist, untwist to remove sensor from opening).

Figure 22:
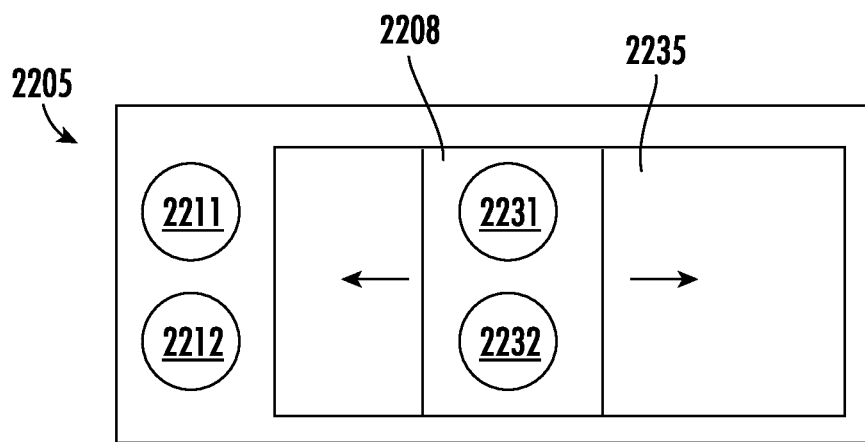
FIG. 22 shows a probe with sensor structures on a moveable slot within the probe.

FIG. 22 shows a probe 2205 with some sensors 2231-2232 (emitters or detectors) on a movable platform 2208. This probe is similar to the probes described in FIGS. 20 and 21 above, where a distance between structures 2211-2212 and structures 2231-2232 can be varied. For probe 2205, structures 2231-2232 are movable by way of sliding the movable platform (e.g., stage, carrier, mechanism, sash, support, or structure) where the structures are situated.

FIG. 22 shows structures 2211-2212 are fixed, while structures 2231-2232 are movable. However, in other implementations, there can be two or more movable structures; and fixed structures can be omitted altogether. By positioning a structure on a movable platform, this allows varying of a distance between two sensors where one is fixed and the other is movable, or each is on different movable platform.

In a specific implementation, structures 2211-2212 are source structures and structures 2231-2232 are detector structures. In another implementation, structures 2211-2212 are detector structures and structures 2231-2232 are source structures.

Compared to probe 2005, by utilizing a sliding mechanism, probe 2205 allows positioning of sensors in a continuous range of positions rather than at discrete positions. In a specific implementation, a user can slide the moveable platform within an opening 2235 (e.g., a slot or groove) in first or second directions as indicated by the arrows to vary a distance with structures 2211-2212. The moveable support can be slid anywhere within the opening and thus allows the distance between structures 2211-2212 and structures 2231-2232 to be infinitely or continuously adjustable.

In other implementations, the moveable platform may be placed in or on a groove, channel, notch, conduit, slide, rail, track, fluid, gel, gears, ball bearings, or similar mechanisms that facilitate sliding of the platform. For example, the grooves or rails may be on a side of the platform or underneath the platform. The moveable platform (holding the sensor structures) may be positioned and placed on rails that allow the platform to move.

Figure 23:
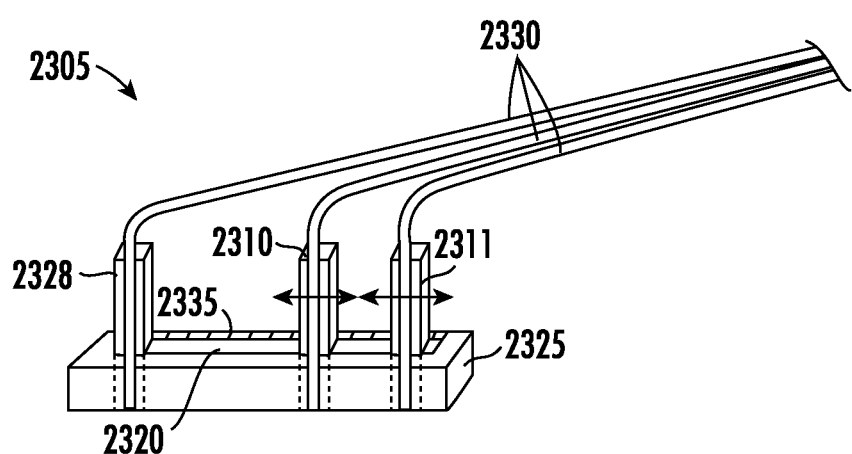
FIG. 23 shows another specific embodiment of a probe with moveable sensors.

In various implementations, there can be any number of moveable supports (e.g., two or more moveable supports). There can be any number of movable supports within a single opening. A probe can have any number of openings in which any number of moveable supports can slide. A structure can be in a fixed position between two openings having moveable supports. FIG. 23 shows a specific implementation of the probe of FIG. 22.

The user may remove and add moveable supports to the opening. For example, the user may remove the moveable support from the opening and replace that previous moveable support with a new moveable support. The new moveable support may include structures of a different type, size, arrangement, number, design, or combinations of these as compared to the structures in the previous moveable support.

A light shading film as shown in FIG. 5 and discussed above may be placed over any of the sensors of probe 2205. The light shading film may be attached to the moveable support, attached to the frame surrounding opening 2235, or both.

Similar to the probe of FIG. 20, probe 2205 can include a mechanism for electronically detecting the position of the moveable platform within opening 2235. For example, the mechanism may include a position sensor that produces a signal that varies as the position of the moveable platform changes within opening 2235. In a specific implementation, the track that the moveable platform slides along includes a material with detectable resistance. As the structure moves along the track, the resistance changes. The change in resistance is used to determine the location or position of the moveable platform within opening 2235 and thus the source and detector separation.

Other examples of position sensors that may be included in various implementations of the probe include inductive sensors, electronic proximity sensors, string potentiometers, linear variable differential transformers, potentiometers, capacitive transducers, eddy-current sensors, Hall effect sensors, optical proximity sensors, grating sensors, and piezoelectric transducers.

FIG. 23 shows a specific embodiment of the probe shown in FIG. 22. A probe 2305 includes two detectors 2310 and 2311, each on a moveable platform. The moveable platforms are within a slot or opening 2320 in a panel 2325. The moveable platforms are positioned lengthwise within the slot. A source 2328 is at positioned at an end of the slot. The source may be in a fixed position or an adjustable position. Cables 2330 are connected to the source and detectors. A set of markings 2335 is adjacent to the slot. The set of markings is similar to the set of markings described above and shown in FIG. 21.

Figure 24:
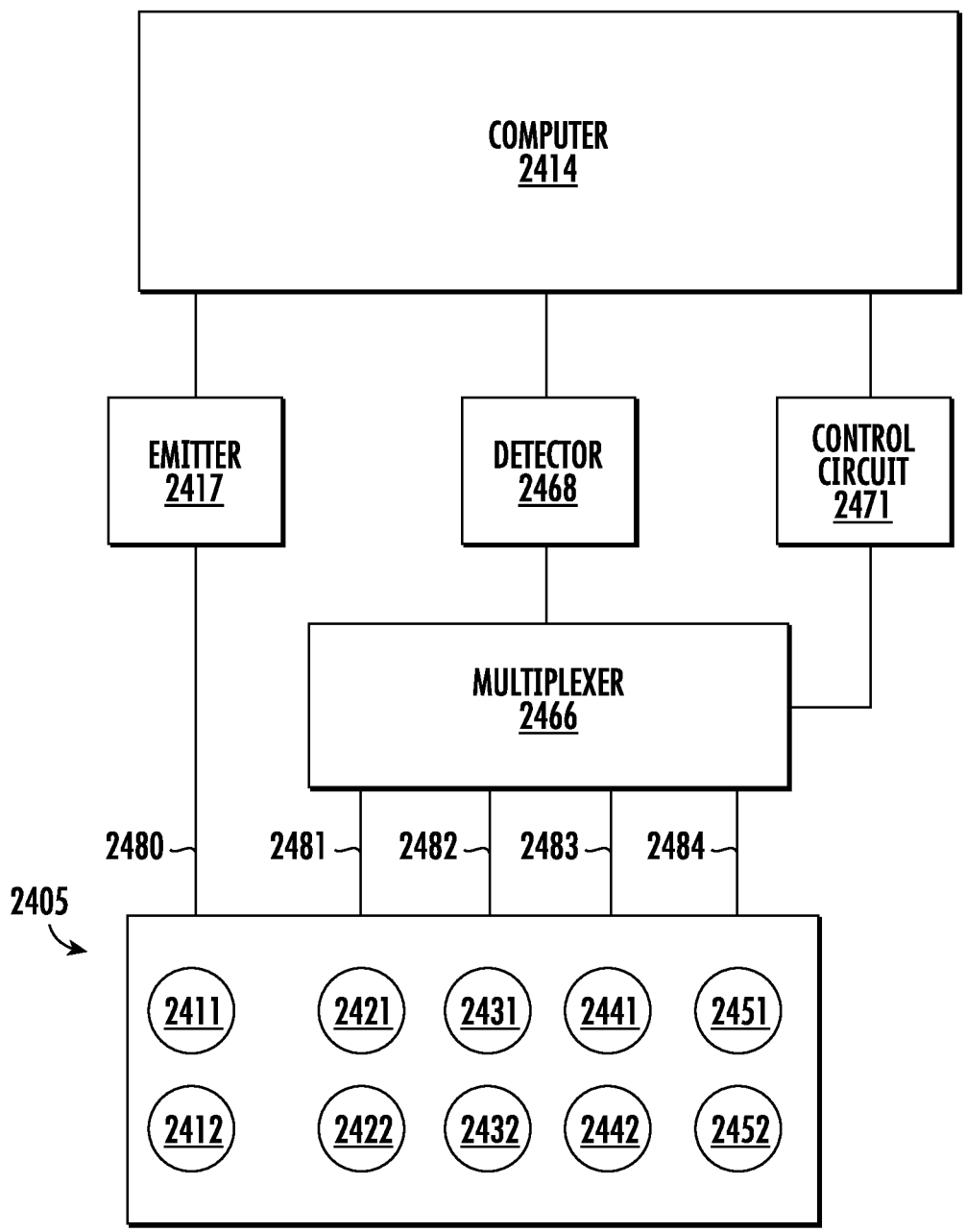
FIG. 24 shows how a multiplexer is used to address each sensor on a probe.

FIG. 24 shows a block diagram of a specific implementation of the invention. A probe 2405 is attached to other components of a tissue oximeter system. The probe has a column 2411-2412 that is connected to a computer 2414 via an emitter 2417. Sensors in columns 2421-2422,2431-2432, 2441-2442, and 2451-2452 are each connected to an input of a multiplexer 2466. The multiplexer is connected to the computer through a detector 2468. The multiplexer has a control input that is connected to a control circuit 2471, which is in turn connected to the computer.

The computer controls operation of the tissue oximeter sensor. To make a measurement using particular source and detector sensors, the computer controls the emitter to emit radiation through sources 2411-2412. This radiation is transmitted into the tissue being evaluated and transmitted or reflected back into detectors 2421-2422,2431-2432,2441-2442, and 2451-2452. The computer, via the multiplexer, controls which detectors to use to evaluate the reflected radiation. For example, the computer can control the control circuit to select the input of the multiplexer corresponding to detectors 2421-2422. Then, the received radiation at these detectors is transmitted through the multiplexer to the detector. The radiation received at other detectors is not transmitted because the multiplexer prevents or blocks their transmission.

The computer receives data about the received radiation from the detector circuit, and using information about the transmitted radiation, performs calculations to determine an oxygen saturation measurement.

Figure 25:
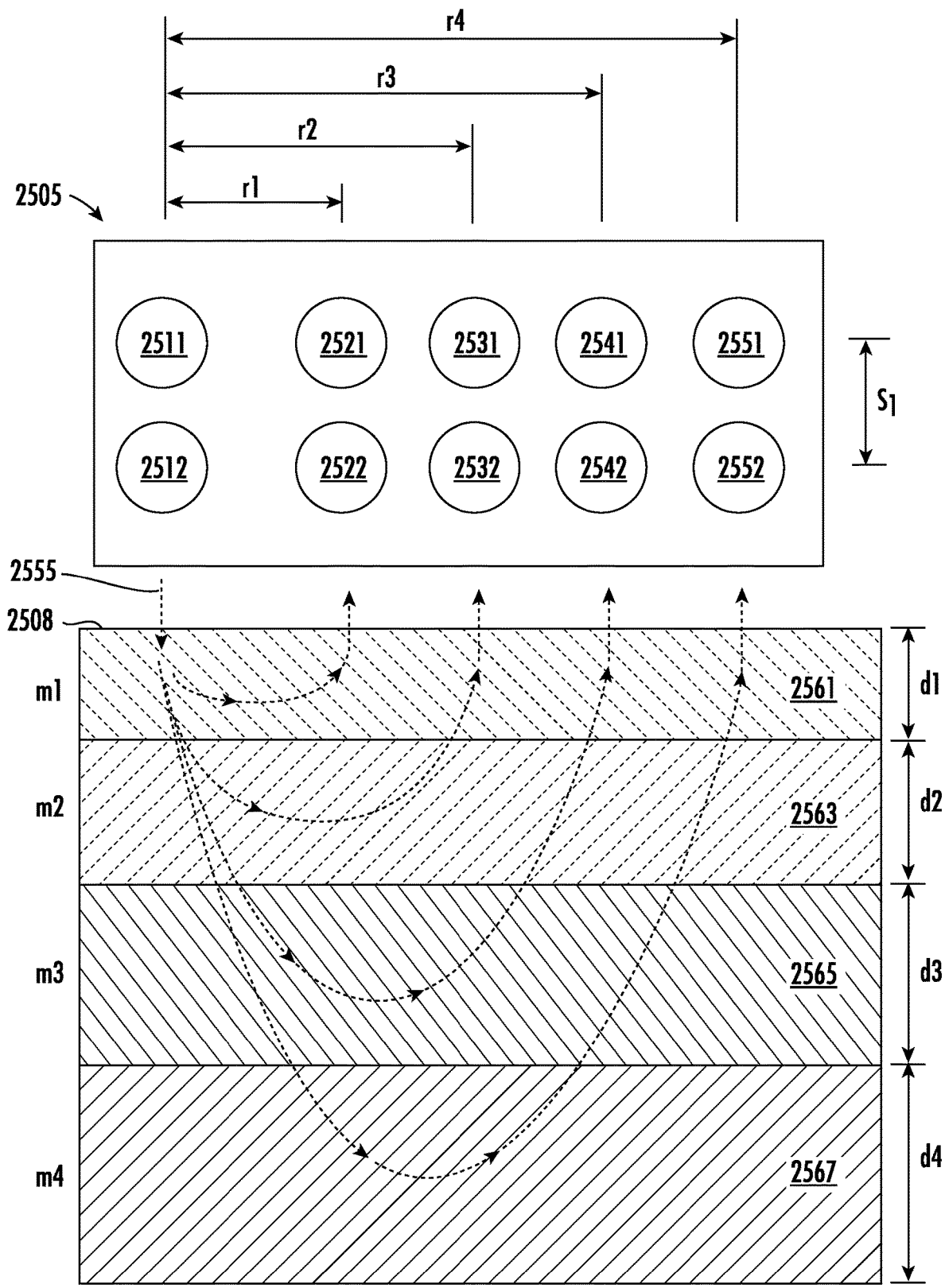
FIG. 25 shows a diagram illustrating a principle for measuring tissue oxygen saturation in different layers of tissue.

Using the circuitry of FIG. 24, a user makes measurements using detectors at varying distances with respect to the fixed sources. This information is used in making oximeter measurements at various tissue depths. The depth of light penetration into the tissue is proportional to the distance of the detector from the source. This principle is shown in FIG. 25. FIG. 25 shows a diagram of light 2555 being transmitted into a tissue 2508. The figure shows how the source and detector spacing (i.e., $r_1$-$r_4$) is used to make measurements at various tissue depths.

Referring now to FIG. 24, although the circuitry shown is for the implementation where the computer via the multiplexer controls which detectors to use, one of skill in the art can make the necessary changes so that the computer via the multiplexer controls instead which sources to use. In short, the detector and source structures are swapped and the emitter and detector are swapped. Thus, in a specific implementation, structures 2411-2412 are detector structures connected to the computer via the detector. Structures 2421-2422, 2431-2432, 2441-2442, and 2451-2452 are source structures connected to the input of the multiplexer. The multiplexer is connected to the computer through the emitter.

In this specific implementation radiation is emitted through the multiplexer. The computer via the multiplexer chooses which source structure will transmit the radiation to the tissue. Radiation is not transmitted from the other source structures because the multiplexer prevents or blocks the transmission. The reflected radiation received by detector structures 2411-2412 and the spacing between the detector and chosen source structures are then used to determine an oxygen saturation measurement.

Multiplexer 2466 is representation of a component that performs the multiplexing function. The multiplexer may be implemented using electrical components (such as transistors, resistors, integrated circuits, and the like) or may be implemented mechanically (such as using switches, gears, pulleys, and the like). The multiplexer may also be implemented using optical fiber, microelectromechanical systems (MEMs), mirrors, and the like. The invention may use any technique, circuit, or device that provides a multiplexing function in order to selectively receive input from (or output to) some structures connected to the multiplexer, but not others.

Signals 2480-2484 can be optical signals, electrical signals, or both. For example, if the structures include optical fiber then the signals will be optical signals. If the structures include LEDs or photodiodes then the signals will be electrical signals.

In an implementation signal 2480 is an optical signal and structures 2411-2412 are source structures including optical fiber. In another implementation signal 2480 is an electrical signal and the source structures include LEDs.

In an implementation signals 2481-2484 are optical signals and structures 2421-2422, 2431-2432, 2441-2442, and 2451-2452 are detector structures including optical fiber. In another implementation, signals 2481-2484 are electrical signals and the detector structures include photodiodes. In a specific implementation, signals 2481-2482 are optical signals and signals 2483-2484 are electrical signals. In this specific implementation, structures 2421-2422 and 2431-2432 include optical fiber and structures 2441-2442 and 2451-2452 include photodiodes.

FIG. 25 is a diagram illustrating how tissue oxygenation measurements can be made for tissue layers at various depths below the surface of a tissue 2508. In this specific implementation, a probe 2505 includes structures 2511-2512 that are sources. Structures 2521-2522, 2531-2532, 2541-2542, and 2551-2552 are detectors. The sources transmit light 2555 into the tissue. A distance $s_1$ indicates the spacing between the rows of structures.

Distances $r_1$-$r_4$ indicate distances from a position where light enters the tissue to a position where light exits the tissue and is received by the detectors. Distance $r_1$ is between structures 2511-2512 and 2521-2522. Distance $r_2$ is between 2511-2512 and 2531-2532. Distance $r_3$ is between 2511-2512 and 2541-2542. Distance $r_4$ is between 2511-2512 and 2551-2552.

This tissue includes four tissue layers. Each layer is at a different depth below a surface of the tissue. A first tissue layer 2561 extends from the surface 2508 to a depth $d_1$. The first tissue layer has an attenuation coefficient $m_1$ and a thickness $d_1$. Below the first tissue layer is a second tissue layer 2563, which has an attenuation coefficient $m_2$ and a thickness $d_2$. Below the second tissue layer is a third tissue layer 2565, which has an attenuation coefficient $m_3$ and a thickness $d_3$. Below third tissue layer is a fourth tissue layer 2567, which has an attenuation coefficient $m_4$ and a thickness $d_4$.

The fourth tissue layer may be considered have an infinite depth or thickness. This means that a bottom of this layer is at about (or beyond) the maximum detectability or visibility range of the system. A maximum depth detectability horizon of a system will depend on a number of factors including the power output of the sources, sensitivity of the detectors, tissue being measured, attenuation factor of the tissue being measured, and other similar considerations. In an implementation, the system can measure up to 40 millimeters below the surface of the tissue, but may be more depending on the situation.

A maximum depth at which a tissue layer lies below the surface of the tissue may be determined by adding the thicknesses of the tissue layers. For example, the second tissue layer is at a depth $d_1+d_2$ below the surface of the tissue.

There can be more or fewer than four layers. By including more or fewer detectors (or sources) at different distances from each other, the probe may be able to give greater or less resolution. For example, a probe with more detectors can make measurements for more layers, so that a given depth of tissue (e.g., 40 millimeters) can be subdivided more finely. So each layer will be thinner. Such a probe and system will give greater resolution.

Also the separation between the detectors (or sensors) will affect the resolution. When a set of detectors are spaced more closely together, this will generally give greater resolution too. And when the set of detectors is spaced further apart, the resolution generally decreases (and also the thickness of the particular layer being measured becomes thicker).

The tissue reflects a portion of the light which is received by the detectors. A detector may receive light from two or more sources. The light may be received concurrently or sequentially. The light generally follows a banana shaped curve as indicated by the dashed lines. The depth of the curve increases with the separation between sources and detectors. Thus, greater separations between sources and detectors allow measuring tissue oxygenation of deep tissue layers while smaller separations allow measuring tissue oxygenation of shallow tissue layers.

In this specific implementation, the structures on the probe are arranged to include four distances (i.e., $r_1$-$r_4$) between the sources and detectors. Thus, this specific implementation of the probe can make tissue oxygenation measurements at four different depths below the surface of the tissue. It should be appreciated that the structures on the probe can be arranged to include any number of distances between the sources and detectors. As discussed above, these distances may be fixed on the probe or the user may adjust the structures on the probe to any desired distance.

As examples, a probe may be arranged such that detector structures 2551-2552 are omitted or inactive such that there are only three distances (i.e., $r_1$-$r_3$). This specific implementation of the probe can make tissue oxygenation measurements at three different depths below the surface of the tissue. As another example, a probe may be arranged such that detector structures 2541-2542 and 2551-2552 are omitted such that there are only two distances (i.e., $r_1$-$r_2$). This specific implementation of the probe can make tissue oxygenation measurements at two different depths below the surface of the tissue.

Distance $s_1$ typically ranges from about 1 millimeter to about 10 millimeters. In various specific implementations, distance $s_1$ is about 1.7 millimeters. Distance $s_1$ is about 5 millimeters. Distance $s_1$ may be about 1.2, 1.4, 1.6, 1.8, 2, 2.5, 3, 3.5, 4, 4.5, 5, 5.5, 6, 6.5, 7, 7.5, 8, 8.5, 9, 9.5, 9.9 millimeters, or more than 9.9 millimeters. In some implementations, distance $s_1$ is less than 1 millimeter.

The following discusses the principle for measuring tissue oxygenation in different tissue layers. First, let us consider the first two shallow layers or the first and second layers. Let $\Gamma(r)$ be the intensity profile and $\Gamma(r)\,dr$ be the probability for a photon to exit from the tissue surface at a distance between r and r+dr from the light source. From a Monte Carlo simulation, $\Gamma(r)$ is given by the approximate expression:

$$\Gamma(r) \approx \frac{1}{4\pi r^2}\left[\sqrt{6m_1}\,e^{-r\sqrt{6m_1}} + \sqrt{6m_2}\,e^{-r\sqrt{6m_2}-y(m_1-m_2)}\right], m_1 > m_2 \quad (1)$$

where $$y = \frac{5.2 d_1}{\sqrt{m_1}}.$$

For the shallow layer, $m_1 = m_2$.

$$\Gamma(r) \approx \frac{1}{2\pi r^2}\sqrt{6m_1}\,e^{-r\sqrt{6m_1}}$$

In the autocalibration scheme, $$\Gamma^{(4)} \approx \left(\frac{r_{12} r_{21}}{r_{11} r_{22}}\right)^2 e^{-(r_{11}-r_{12}+r_{22}-r_{21})\sqrt{6m_1}}$$

Therefore, $$m_1 = \frac{1}{6}\left[\frac{2\ln\frac{r_{12} r_{21}}{r_{11} r_{22}} - \ln\Gamma^{(4)}}{r_{11} - r_{12} + r_{22} - r_{21}}\right]^2 \quad (2)$$

We determine $m_2$ from equation (1) using the $m_1$ calculated from equation (2).

The two-layer model can be applied again to determine $m_3$ while treating the first two shallow tissue layers as the shallow layer in the two-layer model and the third tissue layer as the deep layer in the two-layer model.

Similarly, the two-layer model can be applied again to determine $m_4$ while treating the first three shallow tissue layers as the shallow layer in the two-layer model and the fourth tissue layer as the deep layer in the two-layer model.

Additional discussion is provided in U.S. Pat. No. 6,597,931, issued Jul. 22, 2003, and U.S. patent application Ser. No. 12/116,013, filed May 6, 2008, which are incorporated by reference.

An implementation of the invention may be used for buried flap monitoring. A buried flap may be the result of a free tissue transfer during reconstructive surgery. A free tissue transfer includes removing tissue from one part of the body (i.e., donor site) and transferring the tissue to another part of the body (i.e., recipient site). In some cases, the transferred tissue or flap will be located below the surface of the skin (i.e., buried). The blood vessels of the flap are then anastomosed or connected to the blood vessels at the recipient site. This allows blood to flow into and out of the flap.

A complication in free tissue transfers is thrombosis. That is, clots may form in the blood vessels supplying blood to the flap. If the flap is deprived of blood and thus oxygen then the flap may die. Thus, it is desirable to monitor the buried flap for any ischemia or for any deficient supply of blood to the buried flap. The probe of the invention can be placed on the skin above the buried flap to monitor the tissue oxygen saturation level of the buried flap. Since the buried flap may be located at any depth below the surface of the skin, the system allows the user to select which tissue layer to monitor.

The invention may also be used in other applications where, for example, the tissue of interest is at some depth below the skin. An example includes abdominal organ tissue oxygenation measurement, such as monitoring the tissue oxygen saturation of the liver, kidney, or bowel. Another example includes cerebral oxygenation measurement.

Figure 26:
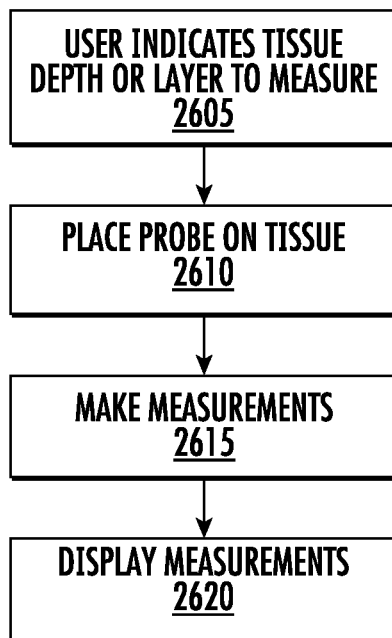
FIG. 26 shows a flow diagram for measuring oxygen saturation of a tissue in an implementation of a probe having fixed structures.

FIG. 26 shows a flow diagram for measuring oxygen saturation of a tissue in a first implementation of the system. This flow diagram can be used for a system including a multiplexer as shown in FIG. 24. In this specific implementation, a probe used in this flow typically includes structures in various fixed positions such as those on probe 2405—FIG. 24 or probe 505—FIG. 5. However, this flow may also be used with a probe that has structures that are moveable using, for example, a mechanically controlled sliding platform, a robotic arm, gear-driven shuttle, or the like.

In a step 2605, the user indicates to the system one or more tissue layers or tissue depths for which the user desires a measurement. For example, for the probe 2405, this probe can make measurements for up to four different layers. So the user, can choose to make measures for any one, any combination, or all the layers. The user indicates his choice by inputting this into the computer, such as via buttons or a touch screen.

Figure 30:
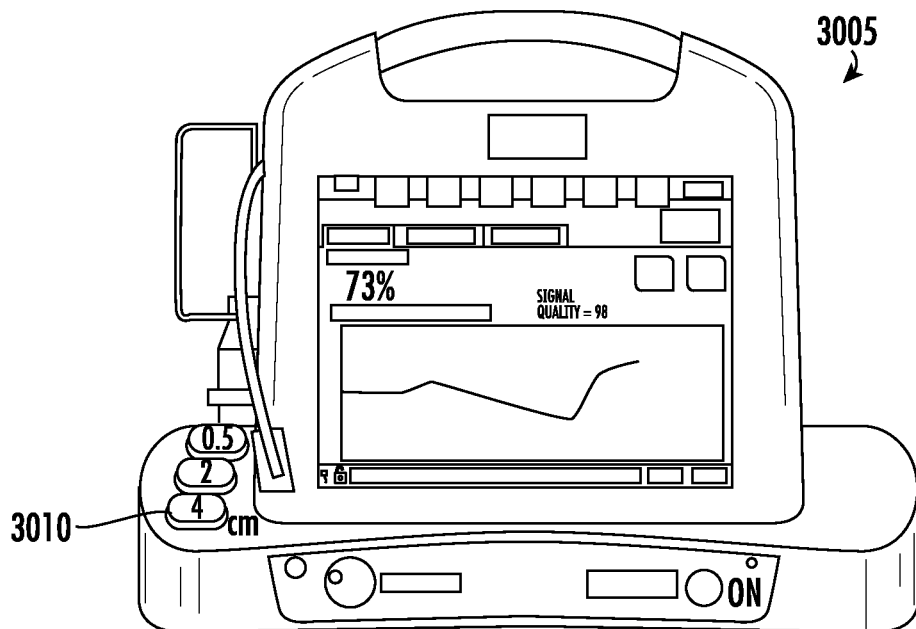
FIG. 30 shows an embodiment of the console where buttons allowing the user to select the desired depth of tissue to monitor are located outside the display of the console.
Figure 31:
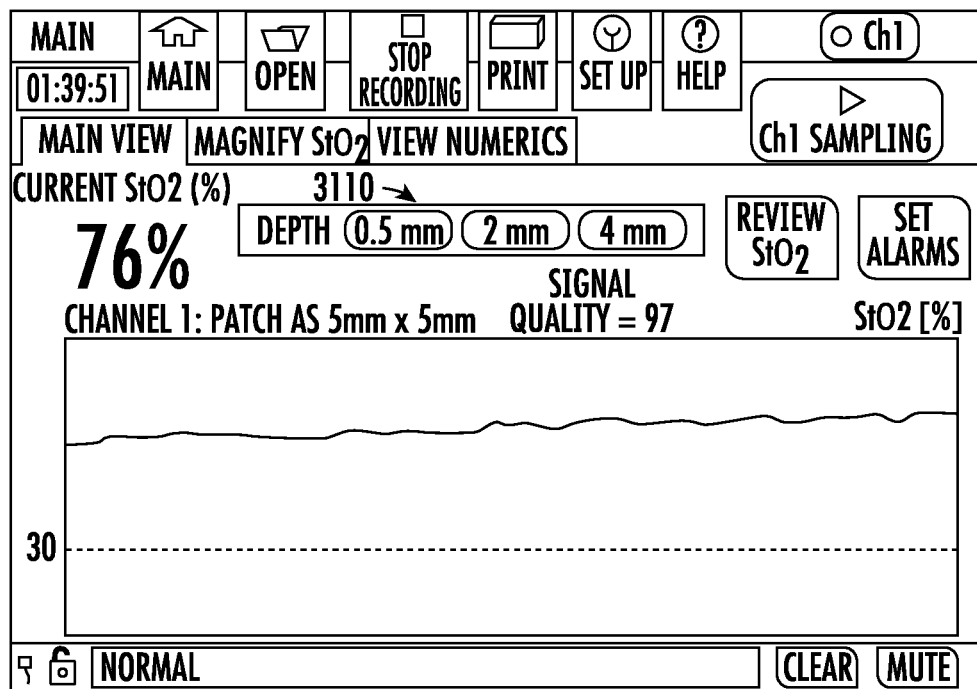
FIG. 31 shows another embodiment of the console where buttons allowing the user to select the desired depth of tissue to monitor are located on a touch screen region of the display.

FIGS. 30-31 show examples of how a user can select a tissue layer or depth to measure. FIG. 30 shows a console 3005 having buttons 3010 on the console. In this specific implementation, these buttons are push buttons (e.g., hard, physical, or mechanical buttons). The user may push a first button labeled 0.5 centimeters to indicate to the system that the user desires to measure a region of tissue 0.5 centimeters below the surface of the tissue; push a second button labeled 2 centimeters to measure a region of tissue 2 centimeters below the surface of the tissue; or push a third button labeled 4 centimeters to measure a region of tissue 4 centimeters below the surface of the tissue.

Another implementation provides a knob that rotates by a specific number of steps.

FIG. 31 shows a technique of using software buttons for the user to input which layer to measure. Buttons 3110 are soft buttons or graphical buttons shown on a touch screen region of the display of the console. The user selects a soft button using a pointing device such as a finger, mouse, or stylus.

In FIGS. 30-31 each button corresponds to one tissue layer or depth. However, in other implementations, a button may correspond to two or more tissue layers or depths. In this specific implementation, selecting the button indicates to the system that the user desires to measure tissue oxygen saturation for two or more tissue layers. For example, for probe 2405 which can make measurements for four layers, there can be four buttons.

Returning to the flow of FIG. 26, in a step 2610, the user places the probe on the tissue where a measurement is desirable. The probe may include an adhesive that allows the probe to be attached to the patient's skin.

In a step 2615, the system makes the measurements by transmitting radiation into the tissue and evaluating the reflected radiation. Using the user's inputted choice of which layers to measure (2605), the system will select the structures to perform the desired measurements using, for example, a multiplexer-type circuit or device. See FIG. 24 and accompanying discussion above.

In a step 2620, after or while the measurements are made, the results are shown on a display of the system. The results can be for the time a measurement is requested or a continuous stream of real-time results.

Figure 27:
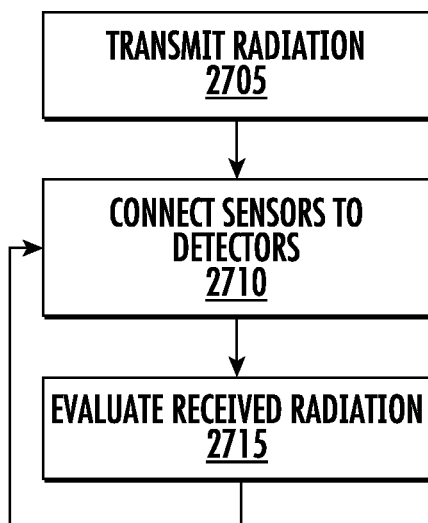
FIG. 27 shows a flow diagram of a specific implementation of using a multiplexer with a specific implementation of a probe having fixed structures.

FIG. 27 shows a flow for a specific implementation of how the system makes measurements (step 2615). In a step 2705, radiation or light is transmitted through the structures of the probe, such as structures 2411-2412 (FIG. 24), into the tissue.

In a step 2710, the system connects sensors (e.g., 2421 and 2422) to detectors (e.g., photodiode detector 2468). In other words, based on the user's desired tissue depth to measure which is received by the system in step 2605, computer 2414 (FIG. 24) via multiplexer 2466 selects the appropriate detectors to use to evaluate the reflected radiation. Thus, in this specific implementation, the user does not have to physically move any structures, sources, or detectors.

In a step 2715, the system evaluates results of the reflected radiation received from the sensors (e.g., 2421 and 2422) with the transmitted radiation (e.g., 2411 and 2412), and calculates an oxygen saturation value. Further details on the measurement techniques were discussed above.

Steps 2710-2715 are repeated as necessary. For example, the user may desire to continuously monitor the tissue for a period of time. Measurements would then typically be made at regular intervals (e.g., every 0.5, 1, 5, 10, 15, or 30 seconds).

Further, the user may desire to monitor two or more tissue layers at the same time. The system can then continuously scan the detectors and evaluate the received radiation from each tissue layer. For example, the user may desire to monitor first and second tissue layers. In an implementation, the system can make one measurement for the first layer, and then make one measurement for the second layer, and alternate back and forth between first and second layers.

More specifically, in step 2710 the system connects sensors to the detectors that receive light from the first tissue layer. In step 2715 the system evaluates the received light and calculates a tissue oxygen saturation for the first tissue layer. The system repeats steps 2710-2715 for the second tissue layer. That is, in step 2710 the system connects sensors to the detectors that receive light from the second tissue layer. In step 2715 the system evaluates the received light and calculates a tissue oxygen saturation for the second tissue layer.

The flow in FIG. 27 may be used for a system as shown in FIG. 24, where computer 2414 controls via multiplexer 2466 which detectors to use. However, a similar flow can also be used for an implementation where the computer controls via the multiplexer which sources to use (e.g., for a probe where the detectors and sources are swapped compared to what is shown in FIG. 24). That is, step 2710 may be replaced by a step in which selected source structures are connected to emitters.

Step 2710 may also be performed by mechanically by, for example, a robotic arm, motor, or actuator. The robotic arm can move the structures (e.g., sources, detectors, or both) to the appropriate position on a probe depending upon the user's desired tissue depth to measure. As an example, if the user desires continuous measurements for two or more layers of tissue (e.g., first and second tissue layers) then the robotic arm will continuously reposition the structures on the probe in order to receive light from the first and second tissue layers.

Figure 29:
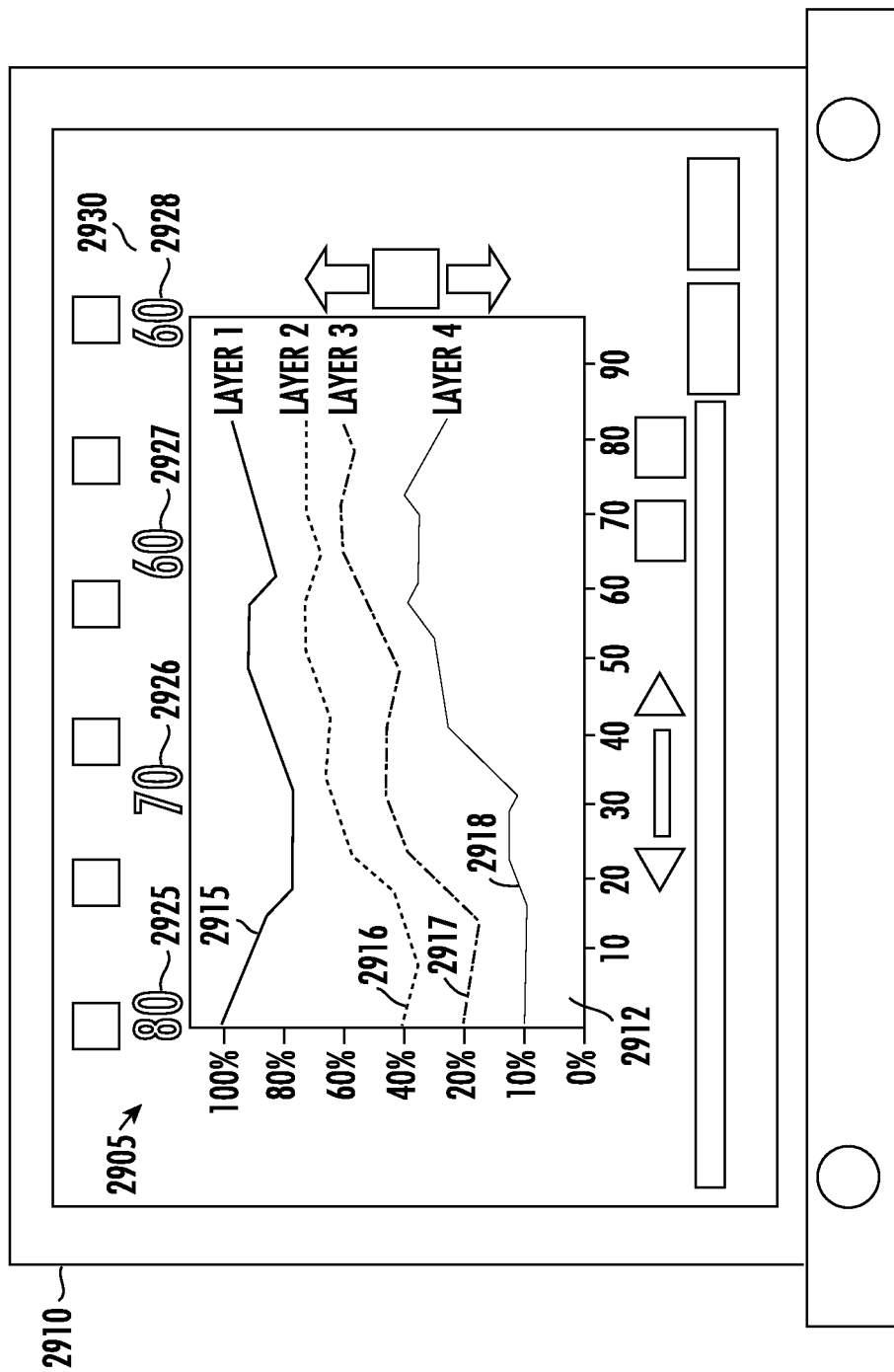
FIG. 29 shows an embodiment of a display of a console where the display includes two or more curves representing tissue oxygenation measurements of different layers of tissue.

As discussed for step 2620 above, the measurement results are displayed to the user. In a specific implementation, the measurements are displayed on a screen of console 2910 as shown in FIG. 29.

The display can show two or more tissue oxygen saturation measurements (e.g., 2925, 2926, 2927, and 2928) where each measurement value represents a different tissue layer or depth. The displayed results can be single shot or a single measurement for one instant in time. Alternatively, the displayed values can change in real time as changes in the measured tissue oxygenation. The values or number for the two or more different layers (measured using the same probe at the same tissue site) can be shown on the display at the same time, so the user does not need to press a button or turn a dial to switch between one layer and another layer.

Further, the displayed results can be curves or trend lines showing tissue oxygenation changes over time for each of the tissue layers, or both. The tissue oxygenation values and the curves can be displayed on the same screen. Or only the tissue oxygenation values may be displayed on the screen, and only the tissue oxygenation curves may be displayed on the screen.

Figure 28:
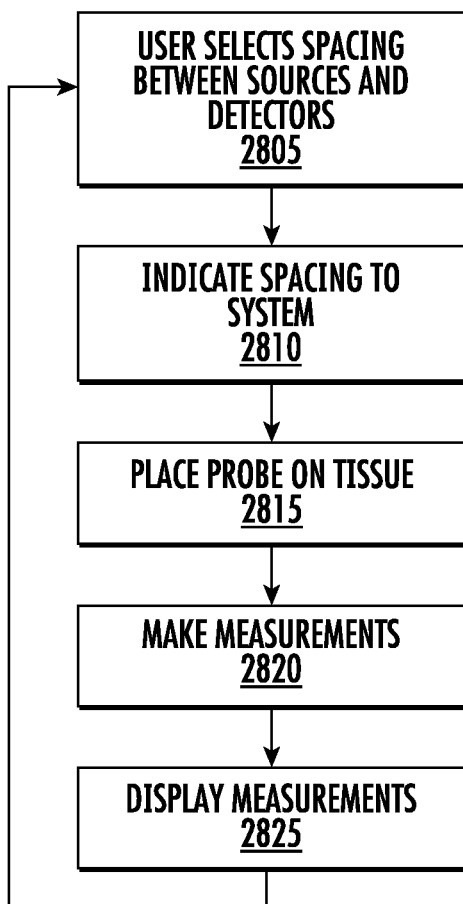
FIG. 28 shows a flow diagram for measuring oxygen saturation of a tissue in another implementation of a probe having moveable structures.

FIG. 28 shows a flow diagram for measuring oxygen saturation of a tissue in a second implementation of the system. A probe in this specific implementation typically includes moveable structures such as those shown in FIGS. 20-23, where the user manually changes the positioning of the sensor structures instead of the system.

In a step 2805, the user physically or manually selects or alters the spacing or distance between the sources and detectors. The user may decrease the spacing between the source and detector structures to make tissue oxygenation measurements at a shallow depth below the surface of the tissue; or increase the spacing to make measurements at a deeper depth below the surface of the tissue.

In a step 2810, the spacing is indicated to the system. In a specific implementation, the user enters at the console the distances between the source and detector structures. As previously discussed, the user may enter the distances using a keypad or other control (e.g., buttons) on the console or other input device, or use soft buttons displayed on a screen.

A probe such as probe 2005 has a number of discrete source and detector positions, which is in contrast to a probe such as probe 2205 which has a continuous range of positions. For probes which have discrete source-detector positions, FIGS. 30-31 show examples of user interfaces for buttons inputting to the system the spacing.

In particular, FIGS. 30-31 show three buttons each labeled with discrete distances. However, in other implementations, other probes discussed in this application such as probe 2205 (FIG. 22) or probe 2305 (FIG. 23) have infinitely or continuously adjustable source and detector separations. In these specific implementations, the buttons may not be labeled with discrete distances corresponding to the source and detector separation since this distance is indeterminate. Instead, in these specific implementations, any specific value can be entered via buttons or controls like a keypad—similar to a keypad on a calculator. This allows the user to indicate to the system any distance.

In another implementation, the probe automatically transmits the distance information to the console. For example, the probe may include a distance measurement sensor which determines the distance between the source and detector structures. Some examples of distance measurement sensors include a linear distance measurement transducer, laser radar, or an interferometer. The distance information may be transmitted wirelessly or through a cable from the probe to the console.

In a specific implementation, as discussed previously, the probe includes a mechanism that automatically detects the position of the sources, detectors, or both. For a probe with discrete source and detector positions (e.g., probes 2005, 2105—FIGS. 20, 21), the mechanism can determine, for example, which openings on the probe are occupied by a sensor, which openings on the probe are not occupied by a sensor (i.e., which openings are empty or vacant), or both. For a probe which has a continuous range of positions (e.g., probes 2205, 2305—FIGS. 22, 23), the mechanism automatically detects the position or location of the sensors on the moveable platform within the slot. This position information is then used by the system to make the tissue oxygenation measurements.

In a step 2815, the user places the probe on the tissue. In a step 2820, the system makes tissue oxygen saturation measurements. Light is transmitted into the tissue. Light reflected from the tissue is received by the detectors. In a specific implementation, the system calculates a tissue oxygen saturation value using the quantities of the radiation transmitted and received and the source and detector spacing indicated to the system by the user (step 2810). Further details may be found in the discussion accompanying FIG. 25.

In a step 2825, the tissue oxygenation measurements are displayed (e.g., displayed on the monitoring console). These steps are then repeated as necessary.

FIG. 29 shows a screen showing multiple oxygen saturation results at multiple depths. Tissue oxygenation measurements 2905 are displayed on a monitoring console 2910. This monitoring console shows in a first region 2912 of the display, four curves 2915-2918 indicating tissue oxygenation measurements over time. Four real time or current tissue oxygenation measurements 2925-2928 are displayed in a second region 2930 of the display.

In a specific implementation, two or more measurements are concurrently shown or superimposed upon each other on the display. Each measurement represents the tissue oxygen saturation for a layer of tissue at a specific depth below the surface of the tissue. A measurement may include a curve representing tissue oxygenation measurements over time, a number indicating current tissue oxygenation measurements, or both.

There can be any combination of tissue oxygen saturation curves and current tissue oxygenation measurements shown on the display depending upon which tissue layer or tissue layers that the user is interested in. Thus, in various implementations, two or more curves and two or more current measurements are shown on the display. Two or more curves are shown and current measurements are not shown (i.e., omitted or hidden). Two or more current measurements are shown and curves are not shown. One curve and two or more current measurements are shown. One current measurement and two or more curves are shown. One curve and one current measurement are shown.

The system includes a control so that the user can select which measurements to display on the console. The control may be a hard or physical button, a soft button or graphical button icon, a dial, a rotating knob, or combinations of these. The controls may be located anywhere on the console. The control may be located outside the display such as on a cabinet or case of the console. The control may be located on the display such as on a touch screen region of the display. The control may be located on a device separate from the console (e.g., remote control). FIG. 30 shows a specific implementation of a console with hard or physical buttons. FIG. 31 shows a specific implementation of a console with soft buttons. FIGS. 30-31 each show a console with three buttons. However, it should be appreciated that a console can include any number of buttons.

Any number of curves can be shown on the display. For example, there can be one, two, three, five, six, seven, or more than seven curves shown on the display depending upon the number of tissue layers that the user desires to measure or monitor.

In a specific implementation, the maximum number of curves that may be displayed depends upon the number of structures of a first type divided by two (e.g., four first type structures then two curves, six first type structures then three curves, and eight first type structures then four curves). In an implementation, the first type includes detector structures. In another implementation, the first type includes source structures.

Typically, the tissue oxygen saturation curves are displayed with a visual indicator so that the user can associate the curve to the region or layer of tissue being measured. In a specific implementation, the visual indicator is a color. In this specific implementation, the first, second, third, and fourth curves are displayed in first, second, third, and fourth colors. The first color is different from the second, third, and fourth colors. The second color is different from the third and fourth colors. The third color is different from the fourth color. These different colors are indicated by the different line patterns.

It should be appreciated that the visual indicator can be anything that visually distinguishes one curve from another curve. Other examples of visual indicators besides colors include different patterns, line weights or thicknesses, blinking patterns or frequencies (e.g., first curve blinks two times per second and second curve blinks five times per second), formatting, or combinations of these.

Text, numbers, or both may be displayed adjacent to the curves to further help the user identify the different tissue layers (e.g., layer 1, layer 2, layer 3, and layer 4) or different tissue depths (e.g., 15 millimeters, 20 millimeters, 30 millimeters, and 40 millimeters) that are being measured.

The system can generate an alert or alarm to indicate to the user a specific status of the monitored tissue. An alert may be generated if the tissue oxygenation measurement exceeds a threshold value, exceeds a threshold value for a threshold period of time, drops or falls below a threshold value, drops below a threshold value for a threshold period of time, or combinations of these. These thresholds (i.e., threshold values and threshold time periods) can be programmed by the user.

Furthermore, the user can assign specific thresholds to each tissue layer. This allows alerts to be generated for a specific tissue layer based on specific thresholds assigned to the tissue layer. For example, the system may display a first warning indicator on a screen of the console if a first oxygen saturation measurement for a first tissue layer drops below a first threshold value. The system may display a second warning indictor on the screen if a second oxygen saturation measurement for a second tissue layer drops below a second threshold value. The first and second threshold values may be different or the same.

The alert may be visual, audible, or both. In a specific embodiment, a visual alert or warning indicator causes a tissue oxygenation value to be displayed differently depending upon whether or not the tissue oxygenation value drops below a threshold value. The tissue oxygenation value may be displayed in a different color, mode (e.g., blinking mode versus solid mode), or combinations of these as compared to a tissue oxygenation value that is above the threshold value.

Other examples of visual alerts or indicia include warning or hazard lights or indicators, alert messages, icons or objects on the display, color coded oxygenation measurements (e.g., measurement displayed in red indicates tissue may die, measurement displayed in green indicates tissue is stable), pattern coded measurements (e.g., blinking pattern, solid pattern, chase or sequential blinking pattern), or combinations of these. Such visual alerts may flash or blink at different frequencies, intensities, brightness levels, or both to indicate different tissue conditions.

Examples of audible alerts include beeps, bells, whistles, chirps, voice (e.g., system plays a recording stating "Tissue layer 2 is low"), or combinations of these. Such audible alerts may sound at different volumes, tones, frequencies, or combinations of these to indicate different tissue conditions.

The first region includes tissue oxygenation percents on a y-axis and time on an x-axis. The percents and time may be displayed using any scale, interval, or increment. For example, the time may be displayed in intervals of 10 minutes, 15 minutes, 1 hour, or 2 hours, and so forth.

Typically, the oxygen saturation curves are shown in a single region (i.e., first region 2912) of the display. However, in another embodiment, each oxygen saturation curve is shown in a separate region of the display. Displaying each curve in a separate region can help the user to distinguish among the different tissue layers being monitored.

Although FIG. 29 shows the tissue oxygenation measurements displayed as curves or line graphs, it should be appreciated that the measurements can be displayed in any type of graph (e.g., pictograph, line plot, pie chart, map chart, histogram, bar graph, frequency polygon, scatter plot, stem and leaf plot, and box plot).

Similar to the curves, real time tissue oxygenation measurements 2925-2928 represent measurements of a specific tissue layer or depth. That is, first real-time measurement 2925 represents a measurement of the first tissue layer. Second real-time measurement 2926 represents a measurement of the second tissue layer. Third real-time measurement 2927 represents a measurement of the third tissue layer. Fourth real-time measurement 2728 represents a measurement of the fourth tissue layer.

In an implementation, the real-time measurements are similarly displayed with the same visual indicator used to display the curves. In another implementation, the visual indicator used for the real-time measurements is different from the visual indicator used for the curves.

The real-time measurements can be displayed anywhere on the display. In an implementation, the real-time measurements are displayed in second region 2930 which is above first region 2912 as shown. In various other implementations, the second region is below the first region, the second region is on a side of the first region (e.g., left-hand side or right hand-side). It should also be appreciated that the second region may at least partially surround the first region. For example, the real-time measurements may be displayed on two or more sides of the first region.

This application describes aspects of the invention in connection with a handheld probe. However, the principles of the invention are also applicable to a probe attached to a tool and implemented as an endoscopic instrument. Endoscopy is a minimally invasive diagnostic medical procedure that is used to assess the interior surfaces of an organ by inserting a tube into the body. At the end of the endoscope tool is a probe as described in this application.

The endoscopic instrument with the probe at the end can have a robotic interface. The robotic interface allows a doctor control the instrument from a remote location. For example, the doctor in New York City can use a tool of the invention to perform a remote procedure on a patient who is located in Barrows, Ak. The doctor will be able to make an oxygen saturation measurement using the probe. The robotic interface may have a haptic interface which provides feedback to the doctor, or may not have a haptic interface. When a haptic interface for the instrument is not available, the readings provided by the instrument may give the doctor an indication of the condition of a tissue.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A device comprising:
   a tissue oximetry probe including a probe surface, which will be placed against a tissue to be measured;
   a first structure of a first type formed on the probe surface;
   a second structure of the first type formed on the probe surface;
   a third structure of a second type formed on the probe surface;
   a fourth structure of the second type formed on the probe surface;
   a fifth structure of the second type formed on the probe surface; and
   a sixth structure of the second type formed on the probe surface, wherein a first distance extends between the first structure and the third structure without touching the second structure or the fifth structure, a second distance extends between the second structure and the fourth structure without touching the first structure or sixth structure, the first distance is different from the second distance, a third distance extends between the first structure and the fifth structure, a fourth distance extends between the second structure and the sixth structure, and the third distance is different from the fourth distance, a first line passing through the third and fourth structures, a second line passing through the fifth and sixth structures, the first line is not collinear with the second line, the third structure comprises an optical fiber and the fourth structure comprises a photodetector, and the probe surface includes the first structure without an intervening structure of the second type between an edge of the probe surface and the first structure.

2. The device of claim 1 wherein the second distance is greater than the first distance, and the fourth distance is greater than the third distance.

3. The device of claim 1 wherein the first line passing through the third and fourth structures is parallel to the second line passing through the fifth and sixth structures.

4. The device of claim 3 wherein a third line passing through the first and second structures is not parallel to the first line.

5. The device of claim 1 wherein a third line passing through the first, third, and fifth structures is parallel with a fourth line passing through the second, fourth, and sixth structures.

6. The device of claim 1 wherein the first type of structure is a source and the second type of structure is a detector.

7. The device of claim 1 comprising:

a first filter associated with the third and fourth structures allows a first spectrum of radiation to pass through to the third and fourth structures; and a second filter associated with the fifth and sixth structures allows a second spectrum of radiation to pass through to the fifth and sixth structures, wherein the first spectrum is different from the second spectrum.

8. The device of claim 7 wherein the first filter comprises a greater attenuation to input radiation than the second filter.

9. The device of claim 7 wherein the first filter comprises greater attenuation at a wavelength range to input radiation than the second filter.

10. The device of claim 7 wherein the first filter and second filter comprise the same attenuation for at least one wavelength for a given radiation input.

11. The device of claim 1 wherein the first line is parallel to the second line.

12. The device of claim 1 wherein a third line passes through the third and fifth structures, and the third line intersects with the first line.

13. The device of claim 12 wherein the third line is transverse with the first line.

14. The device of claim 1 wherein the probe surface includes the second structure without an intervening structure of the second type between the edge of the probe surface and the second structure.

15. The device of claim 1 wherein the first and second structures of the first type are located near a distal end of the probe surface.

16. The device of claim 1 wherein the first and second structures are approximately 0.5 centimeters apart.

17. The device of claim 1 wherein the first and third structures are approximately 4 centimeters apart.

18. The device of claim 1 wherein the first, second, third, fourth, fifth, and sixth structures are used to measure oxygen saturation of tissue.

19. The device of claim 1 wherein for each particular edge of the probe surface, there exists at least one structure of the second type closer to the particular edge than the first and second structures of the first type.

20. The device of claim 1 wherein the tissue oximetry probe placed against tissue is adapted to measure oxygen saturation without pulsing arterial blood.

21. The device of claim 1 wherein the tissue oximetry probe placed against tissue is adapted to measure oxygen saturation without a pulse or a heartbeat.

22. The device of claim 1 wherein the tissue oximetry probe placed against tissue is adapted to measure oxygen saturation for tissue separated from a body of a patient.

23. The device of claim 1 wherein the third and fourth structures are covered by a first film and the fifth and sixth structures are covered by a second film.

24. The device of claim 23 wherein the first and second films comprise films allowing different percentages of light to pass through each respective film.

25. The device of claim 1 wherein a light shading film covers at least one structure of the third, fourth, fifth or sixth structures that is closer to the first or second structure than another structure of the third, fourth, fifth or sixth structures.

26. A device comprising:

a tissue oximetry probe including a probe surface;

a first structure of a first type formed on the probe surface;

a second structure of the first type formed on the probe surface;

a third structure of a second type formed on the probe surface;

a fourth structure of the second type formed on the probe surface;

a fifth structure of the second type formed on the probe surface; and a sixth structure of the second type formed on the probe surface, wherein a first distance extends between the first structure and the third structure without touching the second structure or the fifth structure, a second distance extends between the second structure and the fourth structure without touching the first structure or sixth structure, a first line passing through the third and fourth structures, a second line passing through the third and fifth structures, and the first line intersects with the second line, a light shading film covers the third and fourth structures, the probe surface includes the first structure near a distal end of the device without an intervening structure of the second type between the distal end of the device and the first structure, and at least two of the third, fourth, fifth, or sixth structures comprise an optical fiber and a photodetector.

27. The device of claim 26 wherein the first line and second line are transverse to each other.

28. A device comprising:

a probe surface;

a first structure of a first type formed on the probe surface;

a second structure of the first type formed on the probe surface;

a third structure of a second type formed on the probe surface;

a fourth structure of the second type formed on the probe surface;

a fifth structure of the second type formed on the probe surface; and a sixth structure of the second type formed on the probe surface, wherein a first distance extends between the first structure and the third structure without touching the second structure or the fifth structure, a second distance extends between the second structure and the fourth structure without touching the first structure or sixth structure, a first line passing through the third and fourth structures, a second line passing through the third and fifth structures, and the first line intersects with the second line, a light shading film covers the third and fourth structures, wherein the light shading film does not cover the first, second, fifth, and sixth structures, and the probe surface includes the first structure near a distal end of the device without an intervening structure of the second type between the distal end of the device and the first structure.

29. The device of claim 28 wherein the first line and second line are transverse to each other.

30. The device of claim 28 wherein the device is a tissue oximetry device.

31. The device of claim 28 wherein the first line passing through the third and fourth structures is parallel to the second line passing through the fifth and sixth structures.

32. The device of claim 31 wherein a third line passing through the first and second structures is not parallel to the first line.

33. The device of claim 28 wherein a third line passing through the first, third, and fifth structures is parallel with a fourth line passing through the second, fourth, and sixth structures.

34. The device of claim 28 wherein the first type of structure is a source and the second type of structure is a detector.

35. The device of claim 28 wherein the light shading film allows a first spectrum of radiation to pass through to the third and fourth structures, which is different from a second spectrum of radiation that is allowed to pass through the fifth and sixth structures.

36. The device of claim 28 wherein the light shading film allows a first spectrum of radiation to pass through to the third and fourth structures, which is different from a second spectrum of radiation that is allowed to pass through the first and second structures.

37. The device of claim 28 wherein a third line passes through the third and fifth structures, and the third line intersects with the first line.

38. The device of claim 37 wherein the third line is transverse with the first line.

39. A device comprising:
a tissue oximetry probe including a probe surface;
a first structure of a first type formed on the probe surface;
a second structure of the first type formed on the probe surface;
a third structure of a second type formed on the probe surface;
a fourth structure of the second type formed on the probe surface;
a fifth structure of the second type formed on the probe surface; and
a sixth structure of the second type formed on the probe surface, wherein a first distance extends between the first structure and the third structure without touching the second structure or the fifth structure, a second distance extends between the second structure and the fourth structure without touching the first structure or sixth structure, a first line passing through the first and fourth structures, a second line passing through the third and fourth structures, the first line is parallel to the second line, a third line passing through the first and second structures, the first and third lines do not intersect at a right angle, and the third structure is coupled to an optical fiber and the fourth structure is coupled to an electrical wire.

40. The device of claim 39 wherein a fourth line passes through the fifth and sixth structures, and the second line is parallel to the fourth line.

41. A device comprising:
a probe surface;
a first structure of a first type formed on the probe surface;
a second structure of the first type formed on the probe surface;
a third structure of a second type formed on the probe surface;
a fourth structure of the second type formed on the probe surface;
a fifth structure of the second type formed on the probe surface; and
a sixth structure of the second type formed on the probe surface, wherein a first distance extends between the first structure and the third structure without touching the second structure or the fifth structure, a second distance extends between the second structure and the fourth structure without touching the first structure or sixth structure, a first line passing through the first and fourth structures, a second line passing through the third and fourth structures, the first line is parallel to the second line, a third line passing through the first and second structures, and the first and third lines do not intersect at a right angle, wherein the third structure comprises an optical fiber and the fourth structure comprises a photodetector.

42. A device comprising:
a tissue oximetry probe including a probe surface;
a first structure of a first type formed on the probe surface;
a second structure of the first type formed on the probe surface;
a third structure of a second type formed on the probe surface;
a fourth structure of the second type formed on the probe surface;
a fifth structure of the second type formed on the probe surface; and
a sixth structure of the second type formed on the probe surface, wherein a first distance extends between the first structure and the third structure without touching the second structure or the fifth structure, a second distance extends between the second structure and the fourth structure without touching the first structure or sixth structure, a first line passing through the third and fourth structures, a second line passing through the third and fifth structures, the first line intersects with the second line at a right angle, and the probe surface comprises at least one photodetector and at least one optical fiber.

43. A device comprising:
a tissue oximetry probe including a probe surface, which will be placed against a tissue to be measured;
a first structure of a first type formed on the probe surface;
a second structure of the first type formed on the probe surface;
a third structure of a second type formed on the probe surface;
a fourth structure of the second type formed on the probe surface;
a fifth structure of the second type formed on the probe surface; and
a sixth structure of the second type formed on the probe surface, wherein a first distance extends between the first structure and the third structure without touching the second structure or the fifth structure, a second distance extends between the second structure and the fourth structure without touching the first structure or sixth structure, the first distance is different from the second distance,
a third distance extends between the first structure and the fifth structure, a fourth distance extends between the second structure and the sixth structure, and the third distance is different from the fourth distance,
a first line passing through the third and fourth structures,
a second line passing through the fifth and sixth structures,
the first line is not collinear with the second line, and
the probe surface includes the first structure without an intervening structure of the second type between an edge of the probe surface and the first structure,
wherein a light shading film covers at least one of the third, fourth, fifth or sixth structures, without covering each of the third, fourth, fifth or sixth structures.

44. The device of claim 43 wherein the second distance is greater than the first distance, and the fourth distance is greater than the third distance.

* * * * *